United States Patent
Drmosh et al.

(10) Patent No.: US 11,119,066 B2
(45) Date of Patent: *Sep. 14, 2021

(54) ROOM TEMPERATURE NITROGEN DIOXIDE GAS SENSOR

(71) Applicant: King Fahd University of Petroleum and Minerals, Dhahran (SA)

(72) Inventors: Qasem Ahmed Drmosh, Dhahran (SA); Zain Hassan Yamani, Dhahran (SA); Amar Kamal Mohamedkhair, Dhahran (SA); Abdulmajeed Hasan Hendi, Dhahran (SA); Mohammad Kamal Hossain, Dhahran (SA); Abdullatif Mohammed Albaseer, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 162 days.

This patent is subject to a terminal disclaimer.

(21) Appl. No.: 16/000,438

(22) Filed: Jun. 5, 2018

(65) Prior Publication Data

US 2019/0369040 A1    Dec. 5, 2019

(51) Int. Cl.
G01N 27/12    (2006.01)
G01N 33/00    (2006.01)

(52) U.S. Cl.
CPC ....... *G01N 27/127* (2013.01); *G01N 33/0037* (2013.01)

(58) Field of Classification Search
CPC .......................... G01N 27/127; G01N 33/0037
See application file for complete search history.

(56) References Cited

U.S. PATENT DOCUMENTS 4,399,424 A * 8/1983 Rigby .................... G01N 27/12
                                                 338/308
4,977,658 A * 12/1990 Awano ................ G01N 27/121
                                                 29/25.01

(Continued)

FOREIGN PATENT DOCUMENTS

KR          1027074 B1    4/2011
KR          1498157 B1    3/2015

OTHER PUBLICATIONS

Drmosh, Q. A., et al. ; Gold nanoparticles incorporated SnO thin film: highly responsive and selective detection of NO at room temperature ; Materials Letters vol. 214 ; Mar. 1, 2018 ; Abstract.

(Continued)

*Primary Examiner* — Randy W Gibson
*Assistant Examiner* — Gedeon M Kidanu
(74) *Attorney, Agent, or Firm* — Oblon, McClelland, Maier & Neustadt, L.L.P.

(57) ABSTRACT

A room temperature nitrogen dioxide gas sensor comprising tin(IV) oxide decorated with gold nanoparticles is described. The tin(IV) oxide may have an average layer thickness of 10-1,000 nm, and is topped with dispersed gold nanoparticles having an average longest dimension of 200-650 nm. The room temperature nitrogen dioxide gas sensor may be used to detect and measure levels of nitrogen dioxide gas at room temperature and at concentrations of 100 ppb-1800 ppm, with a high stability. A method of making the room temperature nitrogen dioxide sensor is also described, and involves sputtering to deposit a tin(IV) oxide layer and a gold layer on a substrate, followed by annealing.

20 Claims, 20 Drawing Sheets

(56) References Cited

U.S. PATENT DOCUMENTS

| | | | | |
|---|---|---|---|---|
| 6,044,689 | A * | 4/2000 | Yoshida | G01N 27/12 73/31.03 |
| 7,791,150 | B1 * | 9/2010 | Seal | G01N 33/005 257/414 |
| 8,702,962 | B1 * | 4/2014 | Hunter | G01N 33/004 205/784 |
| 9,383,329 | B2 * | 7/2016 | Usagawa | B82Y 30/00 |
| 2010/0089772 | A1 | 4/2010 | Deshusses et al. | |
| 2010/0212403 | A1 * | 8/2010 | Seal | G01N 33/005 73/31.06 |
| 2010/0310792 | A1 | 12/2010 | Wei et al. | |
| 2013/0186178 | A1 * | 7/2013 | Usagawa | B82Y 15/00 73/31.06 |
| 2013/0199995 | A1 * | 8/2013 | Jiang | B01D 71/70 210/500.27 |
| 2014/0166472 | A1 * | 6/2014 | Ding | C03C 17/3644 204/192.26 |
| 2014/0285224 | A1 * | 9/2014 | Albuschies | G01N 33/48721 324/691 |
| 2016/0216228 | A1 | 7/2016 | Myung et al. | |
| 2019/0003968 | A1 * | 1/2019 | Osawa | G01N 21/6428 |
| 2019/0339227 | A1 * | 11/2019 | Drmosh | C23C 14/086 |

OTHER PUBLICATIONS

Borhaninia, A., et al. ; Gas sensing properties of $SnO_2$ nanoparticles mixed with gold nanoparticles ; Transactions of Nonferrous Metals Society of China 27 ; 2017 ; 8 pages.

Patel, N. G., et al. ; Indium tin oxide (ITO) thin film gas sensor for detection of methanol at room temperature ; Sensors and Actuators B: Chemical ; vol. 96, Issues 1-2 ; Nov. 15, 2003 ; Abstract.

Lee, Ching-Ting, et al. ; Performance Improvement of Nitrogen Oxide Gas Sensors Using Au Catalytic Metal on SnO /WO Complex Nanoparticle Sensing Layer ; IEEE Sensors Journal, vol. 16 Issue 21 ; Aug. 5, 2016 ; Abstract.

* cited by examiner

| Spectrum | In stats. | O | Sn | Au | Total |
|---|---|---|---|---|---|
| Spectrum 1 | Yes | 14.32 | 22.22 | 63.47 | 100.00 |
| Spectrum 2 | Yes | 34.46 | 60.51 | 5.03 | 100.00 |

400 nm

ROOM TEMPERATURE NITROGEN DIOXIDE GAS SENSOR

STATEMENT REGARDING PRIOR DISCLOSURES BY THE INVENTORS

The document, Q. A. Drmosh, Z. H. Yamani, A. K. Mohamedkhair, A. H. Y. Hendi, M. K. Hossain, and Ahmed Ibrahim, "Gold nanoparticles incorporated $SnO_2$ thin film: highly responsive and selective detection of $NO_2$ at room temperature," *Materials Letters* 214, 283-286 (2018), doi: 10.1016/j.matlet.2017.12.013, is herein incorporated by reference in its entirety.

BACKGROUND OF THE INVENTION

Technical Field

The present invention relates to a room temperature nitrogen dioxide gas sensor comprising a $SnO_2$ layer having gold nanoparticles on its surface.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The technological revolution over the last few decades has greatly improved living standards; however, new technologies and increased consumption of resources have propelled more poisonous gases into the environment, causing huge problems for the ecosystem. One such example of poisonous gas includes those of nitrogen oxides ($NO_x$). $NO_x$ gases are classified as a family of hazardous gases and environmental pollutants. Previous reports indicated that the large amounts of $NO_x$ released into the atmosphere everyday cause serious problems to human beings, animals, and plants [Environmental Protection Agency (EPA), Air Pollution, 2011, http://www.epa.gov/air/nitrogenoxides/(accessed 23 Aug. 2011) and L. B. Kreuzer, C. K. N. Patel, "Nitric oxide air pollution: detection by optoacoustic spectroscopy," *Science*, 173 (1971) 45-47—each incorporated herein by reference in their entirety]. Recent scientific studies correlated the negative respiratory effects such as airway inflammation in healthy people, and respiratory problems in asthmatic patients, to short-term exposure to $NO_x$ gases, while pulmonary edema and death are related to the long-term exposure [R. J. Morton, et al., "Exhaled breath condensate nitrite/nitrate and pH in relation to pediatric asthma control and exhaled nitric oxide," *Pediatric Pulmonology* 41 (2006) 929-936, and F. M. Delen, et al., "Increased exhaled nitric oxide in chronic bronchitis," *Chest* 117 (2000) 695-701—each incorporated herein by reference in their entirety]. Nitric oxide (NO) was also found to negatively impact neuron cells, causing neurodegenerative diseases [N. L. R. Han, et al., "Differential mechanisms underlying the modulation of delayed-rectifier K+ channel in mouse neocortical neurons by nitric oxide," *Journal of Neurophysiology* 95 (2006) 2167-2178—incorporated herein by reference in its entirety.]. When exposed to sunlight, $NO_x$ gases in the atmosphere may react with moisture and hydrocarbons to form small particulates, which can then aggravate existing respiratory and heart conditions [R. J. Morton, et al., "Exhaled breath condensate nitrite/nitrate and pH in relation to pediatric asthma control and exhaled nitric oxide," *Pediatric Pulmonology* 41 (2006) 929-936, and F. M. Delen, et al., "Increased exhaled nitric oxide in chronic bronchitis," *Chest* 117 (2000) 695-701—each incorporated herein by reference in their entirety].

In children, the increased risk of developing respiratory diseases and otitis media, and the prevalence of bronchitic symptoms in asthmatic children, is correlated to ambient nitrogen dioxide ($NO_2$) exposure [R. Newhook, et al., "Human Health Risk Assessment for Ambient Nitrogen Dioxide," *Water and Air Quality Bureau Safe Environments Directorate Healthy Environments and Consumer Safety Branch Health Canada*, Minister of Health Canada, 2016, and H. Walton, et al., "Understanding the Health Impacts of Air Pollution in London," Transport for London and the Greater London Authority, 2015, 129 p—each incorporated herein by reference in their entirety]. According to European Environment Agency's air quality in Europe 2016 report, about 71,000 premature deaths per year from 41 European countries could be contributed to $NO_2$ exposure [C. Guerreiro, et al, "Air quality in Europe—2016 report," European Environment Agency, Luxembourg: Publications Office of the European Union, 2016—incorporated herein by reference in its entirety].

$NO_x$ pollution is sourced from cars, trucks, and various non-road vehicles, including ships, boats, and construction equipment, as well as industrial sources such as large industrial operations and power plants. For example, published scientific reports showed that the $NO_x$ emissions in US in year 2005 sourced from on-road vehicles were around 35% of the total annual $NO_x$ emission. Over this same time period, non-automobile fossil fuel combustion and industrial processes contributed around 13% and 6%, respectively [A. Afzal, et al, "Review NOx sensors based on semiconducting metal oxide nanostructures: Progress and perspectives," *Sensors and Actuators B* 171-172 (2012) 25-42—incorporated herein by reference in its entirety]. Another example is the recent inventory of the $NO_x$ emissions in UK carried out in 2011 [United States Environmental Protection Agency, "National Emissions Inventory," www.epa.gov/ttn/chief/net/2011inventory.html—incorporated herein by reference in its entirety]. According to this inventory, on-road gasoline, on-road diesel, and residential oil and gas combustion contributed 28%, 19%, and 7% of the total annual $NO_x$ emission, respectively. Hence, monitoring $NO_2$ is vital for ensuring a clean environment, public health, and responsible industries. This necessitates the development of reliable sensors capable of detecting and monitoring $NO_2$.

Over the past few years, remarkable efforts have been directed towards gas sensing technologies. In particular, metal oxide semiconductor-based gas sensors have been widely utilized for gas detection. As an n-type metal oxide semiconductor, tin dioxide ($SnO_2$) nanostructures exhibit attractive optical, electrical, and chemical characteristics that make them promising candidates for gas sensing applications [Y. Yuan, et al, "Effect of Unsaturated Sn Atoms on Gas-Sensing Property in Hydrogenated $SnO_2$ Nanocrystals and Sensing Mechanism," *Scientific Reports*, 7 (2017) 1231, and L. Chang T Q, et al, "2D tin dioxide nanoplatelets decorated graphene with enhanced performance supercapacitor," *J. Alloys Compd.* 586 (2014) 353-359—each incorporated herein by reference in their entirety]. $NO_2$ chemoresistive gas sensors based on $SnO_2$ nanostructures (nanorods, nanowires, and/or nanotubes) are inexpensive and easy to use, and furthermore have good thermal and chemical stabilities. Unfortunately, however, these $SnO_2$- based sensors only operate well at high temperatures (>200° C.) and have poor selectivity. Also, these $SnO_2$-based sensors are relatively unsuitable for commercialization due to their limited scalability.

Therefore, the most promising $SnO_2$-based gas sensors are those using a thin film structure, due to their long term stability and scalable fabrication [N. V. Toan, et al, "Fabrication of highly sensitive and selective $H_2$ gas sensor based on $SnO_2$ thin film sensitized with microsized Pd islands," *Journal of Hazardous Materials* 301 (2016) 433-42—incorporated herein by reference in its entirety]. However, these sensors still suffer from shortcomings, such as a poor selectivity between gases and the requirement for high operating temperatures [R. K. Sonker, et al., "Low Temperature Operated $NO_2$ Gas Sensor Based on $SnO_2$—ZnO Nanocomposite Thin Film," *Advanced Science Letters* 20 (2014) 911-916, and D. R. Miller, et al, "Nanoscale metal oxide-based heterojunctions for gas sensing: A review," *Sensors and Actuators B* 204 (2014) 250-272—each incorporated herein by reference in their entirety]. High selectivity is necessary to eliminate the interfering resistivity signals resulting from other gas species. In addition, a room temperature gas sensor is attractive due to its low power consumption and low operating cost.

The combination of nanostructured $SnO_2$ with noble metal nanoparticles such as Au nanoparticles has been desirable in many industrial catalytic reactions due to the superior catalytic performance of Au nanoparticles. This catalytic performance is directly related to the nanoparticle dispersion, particle size, and morphology. In the field of chemical gas sensing, the decoration of metal oxides with highly dispersed noble metals has led to a significant enhancement in the selectivity towards target gas and a lowering of the operating temperature [Y. Wang, et al, "Fabrication and gas sensing properties of Au-loaded $SnO_2$ composite nanoparticles for highly sensitive hydrogen detection," *Sensors and Actuators B: Chemical*, 240 (2017), 664-673, and Q. Xiang, et al, "Au Nanoparticle Modified $WO_3$ Nanorods with Their Enhanced Properties for Photocatalysis and Gas Sensing," *J. Phys. Chem. C* 2010, 114, 2049-2055—each incorporated herein by reference in their entirety].

At present, the dispersion of Au nanoparticles over the surface of $SnO_2$ nanorods, nanosheets, and nanobelts is obtained mainly by several chemical methods, including sol gel, precipitation, micro-emulsion methods, etc. [L. Liu, et al., "Synthesis of porous $SnO_2$ hexagon nanosheets loaded with Au nanoparticles for high performance gas sensors," *Materials Letters,* 201 (2017) 211, and C. Jin, "Enhanced ethanol gas sensing properties of $SnO_2$ nanobelts functionalized with Au," *Ceramics International* 38 (2012) 6585— each incorporated herein by reference in their entirety]. These methods mainly involve the use of surfactants or other dispersing agents which can lead to the contamination of the product surface, thus hindering gas sensing applications. Since gas sensing is a surface dominant phenomenon, obtaining uncontaminated and well-dispersed Au nanoparticles over the surface of $SnO_2$ films is desirable for high sensing performance. Therefore, a facile and inexpensive method to resolve the problems of high operating temperatures and poor dispersion of Au nanoparticles over the surface of sputtered $SnO_2$ thin films without using any dispersing reagents is desirable. Such a method is a promising technique to fabricate a $NO_2$ sensor reliably for monitoring and detecting $NO_2$ content in sensitive environments such as hospitals, and more specifically, in premature nursery units.

The Internet of Things (IoT) is a concept that enables various physical objects and methods of communication to achieve a certain task by exchanging information. IoT exploits underlying technologies such as wireless sensor networks, mobile applications, Internet protocols, and ubiquitous, embedded devices to make these objects "smarter" [A. Al-fuqaha, et al., "Internet of Things: A Survey on Enabling Technologies, Protocols and Applications" 17 (2015) 2347-2376—incorporated herein by reference in its entirety]. Nowadays, the IoT has created opportunities for new applications in homes and business, with a strong potential to increase the quality of life and grow the world's economy. For an $NO_2$ gas sensor, IoT is a good field to enable an administrator to remotely monitor and respond to any abnormal gas levels. The collected data from an $NO_2$ gas sensor connected to the Internet may be represented in an application with gas level color coding (such as red, yellow, or green) in order to be easily understood.

In view of the foregoing, one objective of the present invention is to provide a room temperature nitrogen dioxide gas sensor, a method of making, and a method of using to detect nitrogen dioxide gas concentrations through changes in conductivity.

BRIEF SUMMARY OF THE INVENTION

According to a first aspect, the present disclosure relates to a room temperature nitrogen dioxide gas sensor, comprising at least two electrodes on a substrate, the electrodes separated by 100-500 µm; a $SnO_2$ layer in contact with the at least two electrodes on the substrate; and gold nanoparticles dispersed on the $SnO_2$ layer, having an average longest dimension of 200-650 nm.

In one embodiment, the room temperature nitrogen dioxide gas sensor further comprises smaller gold nanoparticles on the $SnO_2$ layer, having an average longest dimension of 10-200 nm.

In one embodiment, the gold nanoparticles have an average nearest neighbor distance of 250-500 nm.

In one embodiment, the $SnO_2$ layer has an average thickness of 10 nm-1,000 nm.

In one embodiment, the $SnO_2$ layer consists essentially of $SnO_2$, and the gold nanoparticles consist essentially of gold.

In one embodiment, the gold nanoparticles are dispersed on the $SnO_2$ layer at a surface density of $2 \times 10^5$-$2 \times 10^{15}$ gold nanoparticles per $m^2$.

In one embodiment, the room temperature nitrogen dioxide gas sensor further comprises a computing device configured to transmit a data measurement.

According to a second aspect, the present disclosure relates to a method of making the room temperature nitrogen dioxide gas sensor of the first aspect. This method involves sputtering $SnO_2$ onto the at least two electrodes on the substrate to produce a $SnO_2$ layer; sputtering gold onto the $SnO_2$ layer to produce a gold layer; and annealing the $SnO_2$ layer and the gold layer at 450-650° C.

In one embodiment, the gold nanoparticles are not contacted with a surfactant or a template.

In one embodiment, for a wavelength in a range of 350-1,000 nm, the $SnO_2$ layer with the gold layer before the annealing has a transmittance of 0.00-0.15, and the room temperature nitrogen dioxide gas sensor has a transmittance of 0.40-0.55.

According to a third aspect, the present disclosure relates to a method of using the room temperature nitrogen dioxide gas sensor of the first aspect. This method involves contacting the gold nanoparticles with a first gas sample; measuring a first resistivity across the at least two electrodes; and determining a response factor, which is the percentage difference of the first resistivity to a second resistivity, relative to the second resistivity. The second resistivity corresponds to a second gas sample comprising nitrogen dioxide gas.

In one embodiment, the second gas sample comprises 100 ppb-1800 ppm nitrogen dioxide gas.

In one embodiment, the first gas sample has a temperature of 0-50° C. and a pressure of 0.9-1.1 atm.

In one embodiment, the first gas sample has a temperature of 20-37° C.

In one embodiment, the first gas sample comprises 300-12,000 ppm of at least one gas selected from the group consisting of $H_2$, $NH_3$, $CO_2$, n-butane, pentane, pentene, $O_2$, and $N_2$.

In one embodiment, the second resistivity has a response time of 30-180 s.

In one embodiment, the first gas sample comprises 0.1-99 vol % of at least one gas selected from the group consisting of $O_2$, $CO_2$, $H_2O$, Ar, and $N_2$, relative to a total volume of the first gas sample, or the first gas sample consists essentially of $O_2$, $CO_2$, $H_2O$, Ar, and/or $N_2$.

In one embodiment, the room temperature nitrogen dioxide gas sensor is located in a neonatal intensive care unit.

In one embodiment, the method further comprises transmitting the response factor, wherein the room temperature nitrogen dioxide gas sensor further comprises a computing device configured to transmit a data measurement.

In one embodiment, the method has a repeatability of at least 99%.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
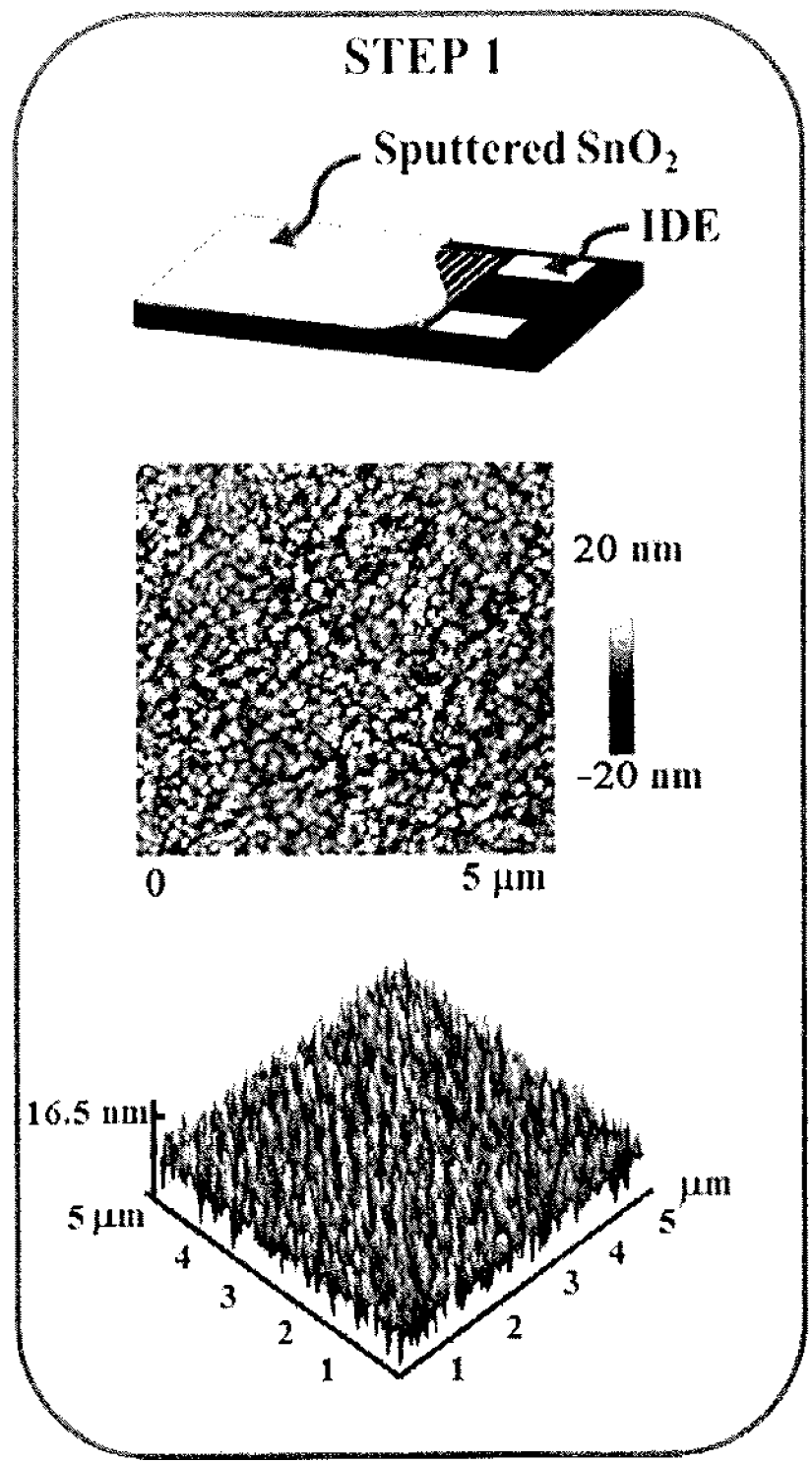
FIG. 1A shows a schematic of a sputtered $SnO_2$ layer with 2D and 3D AFM images.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

As used herein, "compound" is intended to refer to a chemical entity, whether as a solid, liquid, or gas, and whether in a crude mixture or isolated and purified.

As used herein, "composite" refers to a combination of two or more distinct constituent materials into one. The individual components, on an atomic level, remain separate and distinct within the finished structure. The materials may have different physical or chemical properties, that when combined, produce a material with characteristics different from the original components. In some embodiments, a composite may have at least two constituent materials that comprise the same empirical formula but are distinguished by different densities, crystal phases, or a lack of a crystal phase (i.e. an amorphous phase).

The present disclosure is intended to include all hydration states of a given compound or formula, unless otherwise noted or when heating a material. For example, $Ni(NO_3)_2$ includes anhydrous $Ni(NO_3)_2$, $Ni(NO_3)_2 \cdot 6H_2O$, and any other hydrated forms or mixtures. $CuCl_2$ includes both anhydrous $CuCl_2$ and $CuCl_2 \cdot 2H_2O$.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}C$ and $^{14}C$. Isotopes of nitrogen include $^{14}N$ and $^{15}N$. Isotopes of oxygen include $^{16}O$, $^{17}O$, and $^{18}O$. Isotopes of tin include $^{112}Sn$, $^{114-120}Sn$, $^{122}Sn$, and $^{124}Sn$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

According to a first aspect, the present disclosure relates to a room temperature nitrogen dioxide gas sensor. The room temperature nitrogen dioxide gas sensor comprises at least two electrodes on a substrate, a $SnO_2$ layer in contact with the at least two electrodes on the substrate, and gold nanoparticles dispersed on the $SnO_2$ layer.

As described here, "room temperature" may refer to a temperature in a range of 18-24° C., preferably 20-22° C., or about 20° C., or about 25° C. However, in certain cases, and depending on weather, air conditioning, heating, ventilation, and personal preferences, "room temperature" may refer to a temperature lower than 18° C., for example, 15 or 16° C., or to a temperature greater than 24° C., for instance, 27° C. or even 35-37° C. In one embodiment, "room temperature" may refer to more than one temperature in one of the ranges as described previously. For instance, a "room temperature" gas sensor may have a temperature of 20° C., while coming in contact with a "room temperature" gas having a temperature of 22° C. A small difference in temperatures may arise from the gas sensor being attached to a housing, casing, wall, or some other object that has a heat sink effect or a higher heat capacity. In another aspect, the term "room temperature" refers to the ambient temperature of a sample or environment that is in contact with the gas sensor.

In one embodiment, the substrate may be planar, and may have a rectangular shape, a circular shape, or some other shape. In one embodiment, the substrate may have a planar side with a surface area of 0.1-100 $cm^2$, preferably 0.25-50 $cm^2$, more preferably 0.5-10 $cm^2$, even more preferably 0.7-8 $cm^2$. However, in some embodiments, the substrate may have a planar side with a surface area smaller than 0.1 $cm^2$ or larger than 100 $cm^2$. The substrate may have a thickness of 0.10-20 mm, preferably 0.15-15 mm, more preferably 0.17-10 mm, however, in some embodiments, the substrate may have a thickness of less than 0.10 mm, or greater than 20 mm. In an alternative embodiment, the substrate may be curved, grooved, knurled, or shaped into some other non-planar arrangement.

The substrate may be a sapphire substrate, a quartz substrate, a magnesium oxide single crystal substrate, a ceramic substrate, an alumina substrate, a silicon substrate (e.g. silicon wafer or silicon oxide), a silicon nitride substrate, or some other substrate. In one embodiment, the substrate comprises silica ($SiO_2$), and preferably in one embodiment, the substrate consists essentially of silica, meaning that at least 98 wt %, preferably 99 wt %, more preferably at least 99.9 wt % of the substrate is silica, relative to a total weight of the substrate. The silica may be amorphous silica, fumed silica, quartz, or some other type of silica. In alternative embodiments, the substrate may be a type of glass such as flint glass, soda lime glass, or borosilicate glass. In one embodiment, the substrate may be a glass coverslip or a glass slide for a microscope. In an alternative embodiment, the substrate may not necessarily be silica, but may be some other substance having a low electrical conductivity and/or considered an electrical insulator. Defined here, an insulator refers to a solid material with a high electrical resistivity that may prevent an electric current from flowing between two points. The electrical resistivity of the insulator may be at least $10^2$ $\Omega \cdot m$, preferably at least $10^3$ $\Omega \cdot m$, more preferably at least $10^4$ $\Omega \cdot m$ at 20° C.

In one embodiment, the at least two electrodes may be separated by 10-500 μm, preferably 20-450 μm, more preferably 50-300 μm, even more preferably 70-250 μm. In one embodiment, the electrodes may be separated by a minimum distance of the abovementioned ranges. The electrodes may comprise an electrically-conductive material such as indium tin oxide alloy, platinum-iridium alloy, iridium, titanium, titanium alloy, stainless steel, gold, cobalt alloy, copper, aluminum, tin, iron, and/or some other metal or metal alloy. In a preferred embodiment, the electrodes comprise gold. In another preferred embodiment, the electrodes comprise platinum. In other embodiments, the electrodes may comprise a non-metallic electrically-conductive material, such as graphene or a polyelectrolyte. As defined here, an "electrically-conductive material" refers to substance with an electrical resistivity of at most $10^{-6}$ $\Omega \cdot m$, preferably at most $10^{-7}$ $\Omega \cdot m$, more preferably at most $10^{-8}$ $\Omega \cdot m$ at a temperature of 20-25° C. In one embodiment, a part of the electrically conductive material of the electrode may extend away from the substrate in order to connect with a power source to form part of a circuit. In one embodiment, the electrodes may be arranged in an interwoven, interdigitated, or comb-like pattern on the substrate. In one embodiment, two or more interdigitated patterns of electrodes may be electrically connected to each other, forming a continuous, single electrode. In another embodiment, two or more interdigitated electrodes may be electrically isolated from one another, and may function as parallel detector circuits within the room temperature nitrogen dioxide gas sensor. In one embodiment, the at least two electrodes are substantially planar. However, in other embodiments, the electrodes may be located on a surface of a curved or angled substrate, and may be non-planar. In another related embodiment, one or more of the at least two electrodes may be deposited on a location of a substrate having a high surface roughness, for instance an RMS greater than 20 nm, preferably greater than 50 nm, in which the at least two electrodes would not be considered planar. In this case, the electrodes may be formed on nanoparticles or a nano-patterned substrate. In one embodiment, the electrodes may have an average thickness of 100-500 nm, preferably 150-450 nm, more preferably 200-400 nm. The electrodes may be in the form of ribbons, wires, dots, or some other shape.

In one embodiment, the $SnO_2$ layer has an average thickness of 10-1,000 nm, preferably 15-700 nm, more preferably 25-550 nm, even more preferably 40-450 nm or 50-400 nm. However, in some embodiments, the $SnO_2$ layer may have an average thickness of less than 10 nm or greater than 1,000 nm. In one embodiment, the $SnO_2$ layer may have a thickness that varies by less than 50 nm, preferably less than 35 nm, more preferably less than 25 nm of the average thickness. However, in some embodiments, the $SnO_2$ layer may have a thickness in some parts that is more than 50 nm or less than 50 nm of the average thickness.

In one embodiment, the $SnO_2$ layer consists essentially of $SnO_2$, meaning that the $SnO_2$ layer comprises at least 97 wt %, preferably at least 99 wt %, more preferably at least 99.9 wt % $SnO_2$ relative to a total weight of the $SnO_2$ layer. In one embodiment, the $SnO_2$ layer may comprise one or more compounds that are not $SnO_2$, for instance, the $SnO_2$ layer may comprise 1-4 wt %, or 2-3 wt % SnO (tin(II) oxide), relative to a total weight of the $SnO_2$ layer. In other embodiments, other semiconducting metal compounds, metal oxides, or metal sulfides may be used in place of or with the $SnO_2$. These include, but are not limited to, $In_2O_3$, ZnO, $WO_3$, $Co_2O_3$, $TiO_2$, NiO, $ZrO_2$, $Fe_2O_3$, $Al_2O_3$, $Ga_2O_3$, $Nb_2O_5$, and $Sb_2O_3$, $WS_2$, $Bi_2S_3$, or any other semiconducting metal oxide, or a combination of one or more metals including $In_2O_3$ with ZnO, $SnO_2$ with ZnO, or any other combination of metals.

In one embodiment, the $SnO_2$ layer comprises polycrystalline $SnO_2$. "Polycrystalline," as used herein, refers to material composed of multiple crystal grains that are typically separated by high-angle grain boundaries, i.e., boundaries between adjacent grains crystallographically misoriented by greater than 10°, preferably greater than 12°, more preferably greater than 15°. In one embodiment, the polycrystalline $SnO_2$ of the $SnO_2$ layer may be substantially, or even completely, free of any biaxial texture (e.g., a preferred grain-to-grain orientation). However, in other embodiments, the $SnO_2$ layer may comprise amorphous $SnO_2$, or a mixture of polycrystalline and amorphous $SnO_2$.

In one embodiment, the $SnO_2$ layer comprises polycrystalline $SnO_2$ having an average grain size of 5-20 nm, preferably 5.5-15 nm, more preferably 6-10 nm, though in some embodiments, the $SnO_2$ layer may comprise polycrystalline $SnO_2$ having an average grain size of less than 5 nm or greater than 20 nm. In one embodiment, the $SnO_2$ layer may comprise monocrystalline $SnO_2$, or a mixture of amorphous $SnO_2$ and polycrystalline $SnO_2$.

In one embodiment, the grain size may be thought of as the longest distance through a central region of a crystal grain that connects opposite facing surfaces of the crystal grain. In one embodiment, the $SnO_2$ layer may have a lattice parameter or lattice constant (a) of 4.60-4.75 Å, preferably 4.62-4.72 Å, more preferably 4.68-4.70 Å. In one embodiment, the $SnO_2$ layer may have a lattice parameter or lattice constant (c) of 3.16-3.20 Å, preferably 3.16-3.19 Å, more preferably 3.17-3.18 Å. In one embodiment, the $SnO_2$ layer may show X-ray diffraction peaks corresponding to (110), (101), (200), (211), (220), (310), (112), and/or (321) $SnO_2$ crystal faces.

In one embodiment, the gold nanoparticles dispersed on the $SnO_2$ layer may have an average longest dimension or diameter of 200-650 nm, preferably 250-550 nm, more preferably 300-500 nm, even more preferably 320-420 nm. However, in some embodiments, the gold nanoparticles may have an average longest dimension of less than 200 nm or greater than 650 nm. In a further embodiment, a second population of smaller gold nanoparticles may also be dispersed on the $SnO_2$ layer. These smaller gold nanoparticles may have an average longest dimension or diameter of 10-200 nm, preferably 20-180 nm, more preferably 25-160 nm, even more preferably 30-140 nm. However, in other embodiments, the smaller gold nanoparticles may have an average longest dimension or diameter of less than 10 nm or greater than 200 nm. In another embodiment, gold nanoparticles may be embedded within the $SnO_2$ layer and/or dispersed on top of the $SnO_2$ layer.

In one embodiment, the gold nanoparticles may be substantially spherical. As defined here, the term "substantially spherical" means that the standard deviation of the distance from anywhere on the outer surface to the particle centroid (center of mass) varies by less than 30%, preferably by less than 20%, more preferably by less than 10% of the average distance.

In other embodiments, the gold nanoparticles may not be substantially spherical but may instead be elongated, similar to cylinders, ellipsoids, or prisms, having an aspect ratio (length of longest dimension to length of shortest dimension) of 1.10:1-6:1, preferably 1.12:1-5:1, more preferably 1.20-4:1. In one embodiment, the gold nanoparticles may have multiple facets and/or be in the form of plate-like shapes In one embodiment, the gold nanoparticles are monodisperse in size, having a coefficient of variation or relative standard deviation, expressed as a percentage and defined as the ratio of the particle diameter standard deviation ($\sigma$) to the particle diameter mean ($\mu$), multiplied by 100%, of less than 25%, preferably less than 10%, preferably less than 8%, preferably less than 6%, preferably less than 5%. In a preferred embodiment, the gold particles are monodisperse in size, having a particle diameter distribution ranging from 80% of the average particle diameter to 120% of the average particle diameter, preferably 85-115%, preferably 90-110% of the average particle diameter. In another embodiment, the gold particles are not monodisperse in size.

In one embodiment, the gold nanoparticles may be present as agglomerates. As used herein, the term "agglomerates" refers to a clustered particulate composition comprising primary particles, the primary particles being aggregated together in such a way so as to form clusters thereof, at least 50 volume percent of the clusters having an average longest dimension or diameter that is at least 2 times the average longest dimension of the primary particles, and preferably at least 90 volume percent of the clusters having an average longest dimension that is at least 5 times the average longest dimension of the primary particles. The primary particles may be the gold nanoparticles having an average longest dimension as those previously described. In other embodiments, the gold nanoparticles may be shaped like boxes, spikes, flakes, plates, toroids, stars, ribbons, discs, rods, granules, prisms, cones, flakes, platelets, sheets, or some other shape.

In one embodiment, the gold nanoparticles have an average nearest neighbor distance of 250-500 nm, preferably 270-450 nm, more preferably 290-420 nm, even more preferably 320-400 nm. However, in some embodiments, the gold nanoparticles may have an average nearest neighbor distance of less than 250 nm or greater than 500 nm. In one embodiment, the gold nanoparticles being dispersed means that the gold nanoparticles are not agglomerates and have an average nearest neighbor distance of 250 nm or greater.

The gold nanoparticles consist essentially of gold, meaning that the gold nanoparticles comprise at least 97 wt %, preferably at least 99 wt %, more preferably at least 99.9 wt % gold, even more preferably at least 99.99 wt % gold relative to a total weight of the gold nanoparticles. In other embodiments, the gold nanoparticles may not consist essentially of gold, and may be alloys comprising Cu, Ag, or other metals. In one embodiment, both the $SnO_2$ layer consists essentially of $SnO_2$, and the gold nanoparticles consist essentially of gold.

In another embodiment, other metal nanoparticles, including, but not limited to Pt, Pd, and Cu, may be used in place of or in addition to the gold nanoparticles. In one embodiment, the gold nanoparticles are dispersed on the $SnO_2$ layer at a surface density of $2 \times 10^5$-$2 \times 10^{15}$ gold nanoparticles per $m^2$, preferably $2 \times 10^5$-$2 \times 10^{15}$ gold nanoparticles per $m^2$, more preferably $2 \times 10^5$-$2 \times 10^{15}$ gold nanoparticles per $m^2$. However, in some embodiments, the gold nanoparticles may be dispersed on the $SnO_2$ layer at a surface density of less than $2 \times 10^5$ or greater than $2 \times 10^{15}$ gold nanoparticles per $m^2$. In one embodiment, the gold nanoparticles may show X-ray diffraction peaks corresponding to (110), (101), (200), (211), (220), (310), (112), and/or (321) crystal faces.

Preferably, a room temperature nitrogen dioxide gas sensor produces a change in electrical conductivity or resistivity upon exposure to nitrogen dioxide gas. Given Ohm's law, at a fixed electric potential (voltage), the conductivity is inversely proportional to the resistivity. Thus, the room temperature nitrogen dioxide gas sensor may be thought of as detecting a change in conductivity (i.e. current) or a change in resistivity. These changes may result from the adsorption of nitrogen dioxide gas molecules onto the surface of the room temperature nitrogen dioxide gas sensor. In view of that, the room temperature nitrogen dioxide gas sensor may also be referred to as a "chemiresistive nitrogen dioxide gas sensor." However, in other embodiments, the room temperature nitrogen dioxide gas sensor may exhibit other measurable changes in physical properties such as optical transmittance, electrical capacitance, magneto-resistance, photoconductivity, and/or any other detectable property change accompanying the exposure of the room temperature nitrogen dioxide gas sensor to nitrogen dioxide. The room temperature nitrogen dioxide gas sensor may further include a detector constructed and arranged to convert the detectable change of a physical property to a perceivable output, e.g., a visual output, auditory output, tactile output, and/or auditory output.

Figure 14:
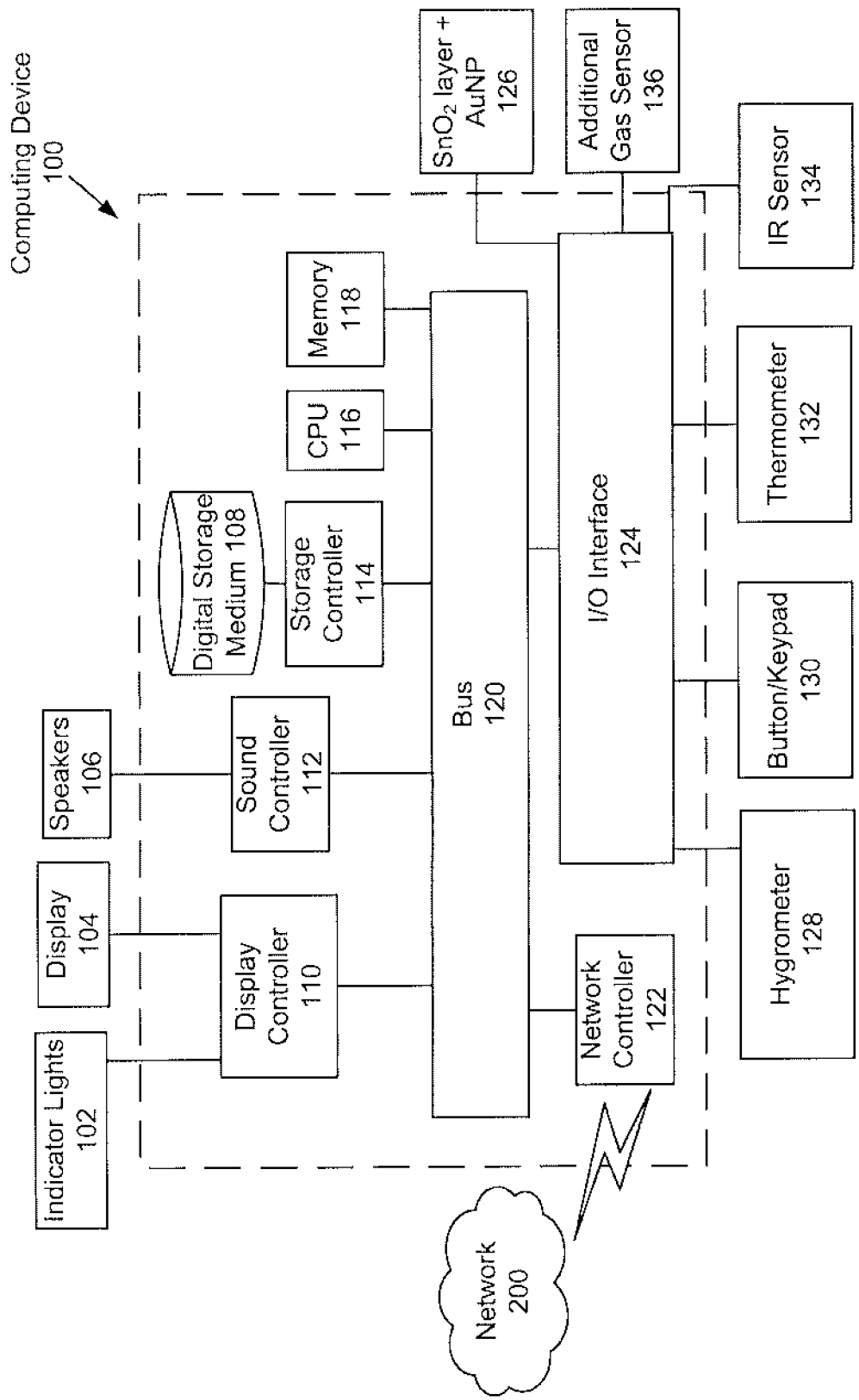
FIG. 14 shows an example of a room temperature nitrogen dioxide gas sensor having a computing device for data collection.

In one embodiment, the room temperature nitrogen dioxide gas sensor further comprises a computing device 100 configured to transmit a data measurement. FIG. 14 shows one embodiment of a computing device 100 that may be used with a room temperature nitrogen dioxide gas sensor. More specifically, the computing device may be connected to the electrodes of the $SnO_2$ layer and gold nanoparticles (AuNP) 126 through an I/O interface 124. In a preferred embodiment, the computing device 100 enables a room temperature nitrogen dioxide gas sensor to transmit data over the Internet, in which the data may be monitored in real time by a desktop computer, a tablet computer, a smart phone, or other mobile or portable electronics.

In one embodiment, the computing device 100 may connect to a battery. The battery may comprise one or more alkaline, lithium, lithium-ion, nickel-cadmium, nickel metal hydride, zinc-air, silver oxide, and/or carbon-zinc electrochemical cells. The electrochemical cells may be wired in parallel, in series, or a combination of both. Preferably the battery is rechargeable. The battery may have a nominal capacity of 10-1500 mAh, preferably 20-1100 mAh, more preferably 30-700 mAh. In an alternative embodiment, computing device 100 does not have a battery and is powered by an AC adaptor or other power source.

In one embodiment, the computing device 100 may connect to one or more indicator lights 102 or a display 104 to indicate nitrogen dioxide levels, alarms, power status, or other information. Where indicator lights are present, preferably the lights are LEDs, though other types of electric lights may be used. In one embodiment, a single, multi-colored light may be used with each color indicating a different level of nitrogen dioxide present. In another embodiment, one or more indicator lights may be scaled by intensity or form a number in order to indicate a level of nitrogen dioxide, and/or a battery capacity.

Where a display 104 is used, the display 104 may comprise one or more LEDs, organic light-emitting diodes (OLEDs), active-matrix organic light-emitting diodes (AMOLEDs), liquid crystal display (LCD) cells, E ink cells, quantum dots, incandescent bulbs, cathode ray tubes, lasers, plasma cells, and/or gas discharge lamps. A display 104 comprising an LCD or E ink element may optionally be backlighted. The display 104 may indicate numeric or alphanumeric information, and may indicate a status of the computing device 100, such as a power state, available storage space, data transfer, network connection, patient name, date, time, case number, operator name, or some other information.

In one embodiment, the display is an LED screen with a plurality of LEDs that form pixels of an image. An LED screen may have a 2D array of at least 625 LEDs, preferably at least 1,000 LEDs, more preferably at least 5,000 LEDs. In one embodiment, the LED display may be similar to a modern computer LED monitor screen, tablet screen, and/or smartphone screen and may produce at least 100 pixels per square inch (PPI), preferably at least 200 PPI, more preferably at least 300 PPI. The image formed may be monochromatic, or multicolored LEDs may be used to produce images of more than one color. The LEDs may be configured to emit light at only one power intensity, or they may be configured to emit light at more than one intensity.

In another embodiment, the computing device may connect with one or more speakers 106 to generate certain sounds or melodies in order to convey similar information relating to levels of nitrogen dioxide. In one embodiment, the one or more speakers 106 may emit a loud alarm if a hazardous level of nitrogen dioxide is detected.

In another embodiment, the computing device 100 may connect to a button or a keypad 130 to set different parameters relating to the room temperature nitrogen dioxide gas sensor and to turn the computing device 100 on or off.

Next, a hardware description of the computing device 100 according to exemplary embodiments is described with reference to FIG. 14. Here, the computing device 100 includes a CPU 116 which performs the processes described above/below. The process data and instructions may be stored in memory 118. These processes and instructions may also be stored on a digital storage medium 108 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk, solid-state drive, and/or any other information processing device with which the computing device communicates, such as a server or computer. In one embodiment, the digital storage medium 108 comprises a memory card that can be removed and exchanged. The digital storage medium of the computing device may have a formatted capacity of 1 MB-10 GB, preferably 10 MB-5 GB, more preferably 100 MB-4 GB.

Further, the claimed advancements may be provided as a utility application, background daemon, or component of an operating system, or combination thereof, executing in conjunction with CPU 116 and an operating system such as Microsoft Windows 7, UNIX, Solaris, LINUX, Apple macOS, and other systems known to those skilled in the art.

The hardware elements of the computing device may be realized by various circuitry elements, known to those skilled in the art. For example, CPU 116 may be a Xenon or Core processor from Intel of America or an Opteron processor from AMD of America, or may be other processor types that would be recognized by one of ordinary skill in the art. Alternatively, the CPU 116 may be implemented on an FPGA, ASIC, PLD, or the CPU may use discrete logic circuits, as one of ordinary skill in the art would recognize. Further, the CPU 116 may be implemented as multiple processors cooperatively working in parallel to perform the instructions of the inventive processes described above and below.

The computing device in FIG. 14 may also include a network controller 112, such as an Intel Ethernet PRO network interface card from Intel of America, for interfacing with a network 200. As can be appreciated, the network 200 may be a public network, such as the Internet, or a private network such as an LAN or WAN network, or any combination thereof, and may also include PSTN or ISDN subnetworks. The network 200 can also be wired, such as an Ethernet network, or can be wireless such as a cellular network including EDGE, 3G, 4G, 5G wireless cellular systems. The wireless network can also be WiFi, Bluetooth, ANT, DASH7, ISA100.11a, MiWi, near-field communication, OCARI, ONE-NET, TSMP, WirelessHART, ZigBee, Z-Wave, and/or any other known form of wireless communication.

The computing device 100 may include a display controller 110, such as a NVIDIA GeForce GTX or Quadro graphics adaptor from NVIDIA Corporation of America. The display controller 110 may interface with a display 104, such as an LED or LCD display. The display controller 110 may also interface with indicator lights 102. A general purpose I/O interface 124 may interface with switches, a keypad, or buttons 130, along with other sensors, such as a $SnO_2$ layer with gold nanoparticles (AuNP) 126 of the present invention, with a hygrometer 128, with a thermometer 132, with an IR sensor 134, or with an additional gas sensor 126. In further embodiments, other sensors relating to health or environmental conditions may also connect with the I/O interface 124.

A sound controller 112 may be provided in the computing device 100, such as Sound Blaster X-Fi Titanium from Creative, to interface with speakers 106 to provide alerting sounds or melodies.

A general purpose storage controller 114 may connect to a digital storage medium 108 with communication bus 120, which may be an ISA, EISA, VESA, PCI, or similar, for interconnecting all of the components of the computing device 100.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

According to a second aspect, the present disclosure relates to a method of making the room temperature nitrogen dioxide gas sensor of the first aspect. This method involves sputtering $SnO_2$ onto the at least two electrodes on the substrate to produce a $SnO_2$ layer; sputtering gold onto the $SnO_2$ layer to produce a gold layer; and annealing the $SnO_2$ layer and the gold layer at 450-650° C.

In one embodiment, the $SnO_2$ layer and/or the gold layer may be deposited by a sol-gel process. The sol-gel process is a versatile solution process for making ceramic and glass materials. In general, the sol-gel process involves the transition of a system from a liquid "sol" (mostly colloidal) into a solid "gel" phase. Applying the sol-gel process, it is possible to fabricate ceramic or glass materials in a wide variety of forms: ultra-fine or spherical shaped powders, thin film coatings, ceramic fibers, microporous inorganic membranes, monolithic ceramics and glasses, or extremely porous aerogel materials. The starting materials used in the preparation of the "sol" are usually inorganic metal salts or metal organic compounds such as metal alkoxides. In a typical sol-gel process, the precursor is subjected to a series of hydrolysis and polymerization reactions to form a colloidal suspension, or a "sol". Further processing of the "sol" enables one to make ceramic materials in different forms. Thin films can be produced on a piece of substrate by spin-coating or dip-coating. When the "sol" is cast into a mold, a wet "gel" will form. With further drying and heat-treatment, the "gel" is converted into dense ceramic or glass articles. If the liquid in a wet "gel" is removed under a supercritical condition, a highly porous and extremely low density material called "aerogel" is obtained. As the viscosity of a "sol" is adjusted into a proper viscosity range, ceramic fibers can be drawn from the "sol." Ultra-fine and uniform ceramic powders are formed by precipitation, spray pyrolysis, or emulsion techniques. In one embodiment, the $SnO_2$ and/or the gold may be deposited by electron beam deposition, chemical vapor deposition, wet deposition, or some other technique. In one embodiment, the $SnO_2$ and/or the gold may be sputtered, for instance, by a RF sputtering mode, a magnetron sputtering mode, or a DC sputtering mode. In one embodiment, the $SnO_2$ is sputtered by a RF sputtering mode, and the gold is sputtered by a DC sputtering mode.

Where the $SnO_2$ and/or gold are sputtered, a sputtering chamber may be used that is evacuated to a base pressure of less than $3.5 \times 10^{-6}$ Torr, preferably less than $3.0 \times 10^{-6}$ Torr. Then, the sputtering chamber may be filled with argon gas, or a gas mixture comprising 5-20 vol %, preferably 10-18 vol %, more preferably 12-16 vol % oxygen in argon gas, relative to a total volume of the gas mixture. The pressure of the argon or the gas mixture (i.e. working pressure) may be maintained in the range of 0.5-10 mTorr, preferably 1-6 mTorr in the sputtering chamber during sputtering. A sputtering power may be set to a value in the range of 10 to 500 W, preferably 20 to 300 W. An $SnO_2$ source may be used for sputtering the $SnO_2$ onto the substrate, and a gold source may be used for sputtering the gold onto the $SnO_2$. The distance between the target and the substrate may be 5-20 cm, preferably 7-15 cm, more preferably 8-12 cm. The substrate may be maintained at room temperature, or at 20-37° C., preferably 22-32° C., more preferably 26-30° C. In one embodiment, the $SnO_2$ may be sputtered for 0.5-4 h, preferably 1-3 h, more preferably 1.25-2.0 h, and the gold may be sputtered for 15 s-2 min, preferably 30 s-1.5 min, or 40-60 s.

Following the deposition of the $SnO_2$ and gold, the $SnO_2$ layer and the gold layer may be annealed in an oven at a temperature of 450-650° C., preferably 480-640° C., more preferably 520-620° C., even more preferably 550-615° C., to produce the room temperature nitrogen dioxide gas sensor. However, in some embodiments, the annealing may be carried out at temperatures lower than 450° C., such as 425° C., or greater than 650° C., such as 680-700° C. The $SnO_2$ layer and the gold layer may be annealed in an atmosphere of air, or in an atmosphere consisting essentially of an inert gas, such as $N_2$ or argon.

In one embodiment, the annealing may be carried out for 0.5-5 hours, preferably 0.6-4 hours, more preferably 0.75-1.5 hours, or about 1 hour, however, in some embodiments, the annealing may be carried out for less than 30 minutes or greater than 5 hours. In a preferred embodiment, the annealing is carried out for 0.75-1.5 hours. In one embodiment, for the annealing step, the $SnO_2$ layer and the gold layer may be placed in an oven heated at 450-650° C. or any of the above annealing temperature ranges. In another embodiment, the $SnO_2$ layer and the gold layer may be placed in an oven at room temperature, and then heated to one of the above annealing temperatures at a rate of 1-20° C./min, preferably 5-18° C./min, more preferably 12-16° C./min, or about 15° C./min. However, in some embodiments, the oven may be heated at a rate slower than 1° C./min or faster than 20° C./min. In one embodiment, following the annealing time, the oven may be turned off with the room temperature nitrogen dioxide gas sensor inside and allowed to cool to room temperature. In another embodiment, the room temperature nitrogen dioxide gas sensor may be taken out and placed in a room temperature environment in order to cool. In another embodiment, the room temperature nitrogen dioxide gas sensor may be cooled with a stream of inert gas, such as nitrogen or argon.

In one embodiment, the gold nanoparticles are not contacted with a surfactant or a template. Here, the gold nanoparticles are formed in a dispersed arrangement on the $SnO_2$ layer by the annealing step. However, in an alternative embodiment of a method of making, a surfactant or template may be used to disperse the gold nanoparticles. A surfactant or template may be an ionic surfactant, a nonionic surfactant, or a biological surfactant.

Exemplary ionic surfactants include, but are not limited to, (1) anionic (based on sulfate, sulfonate or carboxylate anions), for example, perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate (SLES)), alkyl benzene sulfonate, soaps, and fatty acid salts; (2) cationic (based on quaternary ammonium cations), for example, cetyl trimethylammonium bromide (CTAB) (also known as hexadecyl trimethyl ammonium bromide), and other alkyltrimethylammonium salts, cetylpyridinium chloride (CPC), polyethoxylated tallow amine (POEA), benzalkonium chloride (BAC), and benzethonium chloride (BZT); and (3) zwitterionic (amphoteric), for example, dodecyl betaine, cocamidopropyl betaine, and coco ampho glycinate.

Exemplary nonionic surfactants include, but are not limited to, alkyl poly(ethylene oxide), alkylphenol poly(ethylene oxide), copolymers of poly(ethylene oxide) and poly (propylene oxide) (commercially known as Poloxamers or Poloxamines), polyoxyethylene octyl phenyl ether (TRITON X-100®), alkyl polyglucosides, for example, octyl glucoside and decyl maltoside, fatty alcohols, for example, cetyl alcohol and oleyl alcohol, cocamide MEA, cocamide DEA, and polysorbates (commercially known as TWEEN 20, TWEEN 80), for example, dodecyl dimethylamine oxide.

Exemplary biological surfactants include, but are not limited to, micellular-forming surfactants or surfactants that form micelles in solution, for example, DNA, vesicles, phospholipids, and combinations thereof. In other embodiments, other additives or templates may be used to direct the dispersion of the gold nanoparticles, such as polyethylene glycol, dopamine, sodium citrate, or some other polymer.

In one embodiment, where the substrate comprises transparent silica, preferably quartz or glass such as a quartz slide or a glass slide, the room temperature nitrogen dioxide gas sensor has a transmittance of 0.40-0.55, preferably 0.42-0.52, more preferably 0.45-0.50, for a wavelength in a range of 350-1,000 nm, preferably 400-800 nm, more preferably 450-750 nm. However, in other embodiments, the room temperature nitrogen dioxide gas sensor has a transmittance of less than 0.40 or greater than 0.55, and in other embodiments, the room temperature nitrogen dioxide gas sensor may have a transmittance of those previously discussed for a wavelength of less than 350 nm or greater than 1,000 nm.

Likewise, in another embodiment, where the substrate comprises transparent silica, preferably quartz or glass such as a quartz slide or a glass slide, the $SnO_2$ layer and the gold layer (which may otherwise be considered the room temperature nitrogen dioxide gas sensor in progress, before the annealing step) together have a transmittance of 0.00-0.15, preferably 0.01-0.12, more preferably 0.05-0.10, for a wavelength in a range of 350-1,000 nm, preferably 400-800 nm, more preferably 450-750 nm. Here, a transmittance of 0.15 and less may be considered opaque or mostly opaque, with a transmittance of exactly 0.00 being completely opaque, where no light is able to pass through. However, in other embodiments, the $SnO_2$ layer and the gold layer together have a transmittance of greater than 0.15, for instance, 0.16-0.30, or 0.18-0.25. In other embodiments, the $SnO_2$ layer and the gold layer together may have a transmittance as those previously discussed for a wavelength of less than 350 nm or greater than 1,000 nm. In one embodiment, the reduction in opacity (or, the increase in transmittance and transparency) results from the annealing step converting the gold film into gold nanoparticles.

According to a third aspect, the present disclosure relates to a method of using the room temperature nitrogen dioxide gas sensor of the first aspect. This method involves contacting the gold nanoparticles with a first gas sample, measuring a first resistivity across the at least two electrodes, and determining a response factor. Here, the second resistivity is decreased by 70-99.9% relative to a first resistivity arising from a first gas sample, where the first gas sample is substantially free of nitrogen dioxide gas. The first gas sample may be measured before and/or after the second gas sample. In some embodiments, the first gas sample may be considered a gas blank sample, as it is intended to not produce a detection signal as would as gas sample comprising nitrogen dioxide gas. In some embodiments, the second resistivity is decreased by 75-95%, preferably 78-92%, more preferably 80-90% relative to a first resistivity. In some embodiments, the second resistivity is decreased by 10-75%, preferably 20-60%, more preferably 30-50% relative to a first resistivity. However, in some embodiments, the second resistivity may be decreased by smaller than 10% or larger than 99.9% relative to a second resistivity. The response factor is the percentage difference of the first resistivity to a second resistivity, relative to the second resistivity. The second resistivity corresponds to a second gas sample comprising nitrogen dioxide gas. For instance, in one embodiment, a nitrogen dioxide gas concentration of 1-20 ppm may produce a response of 40-85%, preferably 50-82%, more preferably 70-80%. A nitrogen dioxide gas concentration of 20-35 ppm may produce a response of 65-95%, preferably 70-90%. A nitrogen dioxide gas concentration of 35-60 ppm may produce a response of 70-97%, preferably 75-96%, more preferably 78-95%. A nitrogen dioxide gas concentration of 60-100 ppm may produce a response of 75-99.9%, preferably 80-99%, more preferably 92-98%.

In one embodiment, the first gas sample and/or the second gas sample has a temperature of 0-50° C., preferably 15-40° C., more preferably 20-37° C., even more preferably 22-28° C. However, in some embodiments, the first gas sample and/or the second gas sample may have a temperature of less than 0° C. or greater than 50° C.

In one embodiment, the first gas sample may have a total pressure of 0.9-1.1 atm, preferably 0.92-1.08 atm, more preferably 0.95-1.05 atm. However, in some embodiments, the first gas sample may have a total pressure of less than 0.9 atm or greater than 1.1 atm.

In one embodiment, the first gas sample comprises 300-12,000 ppm, preferably 500-10,000 ppm, more preferably 1,000-6,000 ppm of at least one gas selected from the group consisting of $H_2$, $NH_3$, $CO_2$, n-butane, pentane, pentene, $O_2$, and $N_2$. However, in other embodiments, the first gas sample may comprise at least one of the previously mentioned gases at a concentration of less than 300 ppm or greater than 12,000 ppm.

In one embodiment, the first gas sample comprises 0.1-99 vol %, preferably 1-90 vol %, more preferably 10-80 vol %, even more preferably 15-70 vol %, or 20-60 vol %, or 0-10 vol %, 10-20 vol %, 20-30 vol %, 30-40 vol %, 40-50 vol %, 50-60 vol %, 60-70 vol %, 70-80 vol %, 80-90 vol %, 90-99 vol % of at least one gas selected from the group consisting of $O_2$, $CO_2$, $H_2O$, Ar, and $N_2$, relative to a total volume of the first gas sample. In another embodiment, the first gas sample consists essentially of $O_2$, $CO_2$, $H_2O$, Ar, and/or $N_2$. Where the first gas sample consists essentially of $O_2$, $CO_2$, $H_2O$, Ar, and/or $N_2$, the first gas sample may comprise 99.999 vol %, preferably 99.9999 vol %, more preferably 99.99999 vol % of $O_2$, $CO_2$, $H_2O$, Ar, and/or $N_2$ relative to a total volume of the first gas sample. In other words, where the first gas sample consists essentially of $O_2$, $CO_2$, $H_2O$, Ar, and/or $N_2$, the first gas sample comprises $O_2$, $CO_2$, $H_2O$, Ar, and/or $N_2$ and less than 100 ppm of other gases, preferably less than 10 ppm of other gases, more preferably less than 1 ppm of other gases. In one embodiment, the first gas sample may be air, for example, from an indoor or outdoor environment. The air may comprise 75-80 vol % $N_2$, 18-22 vol % $O_2$, 0-1.2 vol % Ar, 0-0.05 vol % $CO_2$, and 0-2 vol % $H_2O$.

In one embodiment, the second gas sample comprises 100 ppb-1800 ppm nitrogen dioxide gas, preferably 500 ppb-1,000 ppm nitrogen dioxide gas, more preferably 1 ppm-600 ppm nitrogen dioxide gas, even more preferably 5 ppm-500 ppm nitrogen dioxide gas. However, in some embodiments, the second gas sample may comprise less than 100 ppb or more than 1800 ppm nitrogen dioxide gas.

In one embodiment, the second gas sample may have a total pressure of 0.9-1.1 atm, preferably 0.92-1.08 atm, more preferably 0.95-1.05 atm. However, in some embodiments, the second gas sample may have a total pressure of less than 0.9 atm or greater than 1.1 atm.

In one embodiment, the room temperature nitrogen dioxide gas sensor is located in a neonatal intensive care unit (NICU). The definition of a neonatal intensive care unit (NICU) according to the National Center for Statistics is a "hospital facility or unit staffed and equipped to provide continuous mechanical ventilatory support for a newborn infant." Neonatology and NICUs have greatly increased the survival of very low birth-weight and extremely premature infants. In the era before NICUs, infants of birth weight less than 1400 grams (3 lb, usually about 30 weeks gestation) rarely survived. Today, infants of 500 grams at 26 weeks have a fair chance of survival. Common diagnoses and pathologies in the NICU include anemia, apnea, bradycardia, bronchopulmonary dysplasia (BPD), hydrocephalus, intraventricular hemorrhage (IVH), jaundice, necrotizing enterocolitis (NEC), patent ductus arteriosus (PDA), periventricular leukomalacia (PVL), infant respiratory distress syndrome (RDS), retinopathy of prematurity (ROP), neonatal sepsis, and transient tachypnea of the newborn (TTN).

Neonates cared for in a neonatal intensive care may be carefully monitored for body temperature, respiration, cardiac function, oxygenation, and brain activity. They may be administered medications, and provided nutrition through intravenous catheter or NG tubes. Additional equipment used to evaluate and treat sick neonates may be used in conjunction with an incubator, or within an NICU include blood pressure monitors, oxygen hoods, and ventilators.

In a further embodiment, the room temperature nitrogen dioxide gas sensor may be located within a crib or an incubator, to monitor and alert for nitrogen dioxide gas as soon as an infant may be exposed. An incubator (or isolette) is an apparatus used to maintain environmental conditions suitable for a neonate (newborn baby). It is used in preterm births or for some ill full-term babies.

A neonatal incubator may be used to assist in oxygenation, for instance, through oxygen supplementation by head hood or nasal cannula, continuous positive airway pressure (CPAP), or mechanical ventilation. Infant respiratory distress syndrome is the leading cause of death in preterm infants, and the main treatments are CPAP, in addition to administering pulmonary surfactant and stabilizing blood sugar, blood salts, and blood pressure.

Incubators may provide additional protection from cold temperatures, dryness, infection, noise, drafts, and excess handling. Incubators may be described as bassinets enclosed in plastic, with climate control equipment designed to stabilize temperature and limit germ exposure. Incubators may also maintain a neonate's fluid balance by providing fluid and keeping a high air humidity to prevent too great a loss of moisture from skin and respiratory evaporation.

In other embodiments, the room temperature nitrogen dioxide gas sensor may be contacted with a gas sample that originates from an ambient indoor environment, for example, of a residence, a factory, a store, a hospital, a car, an air duct, or some other indoor environment. In another embodiment, a gas sample may come from an outdoor environment such as a highway, road tunnel, or city street, or from a cave, a mine, a subway station or a geothermal vent. In another embodiment, a gas sample may come from a vessel or tubing of a laboratory or a chemical processing plant, where nitrogen dioxide may be a main product, a byproduct, or a contaminant.

In one embodiment, the room temperature nitrogen dioxide gas sensor may be located at the source of the gas sample, or it may be located away from the gas sample, and a gas sample may be collected and contacted with the sensor. In a related embodiment, the gas sample may be diluted, concentrated, pressurized, depressurized, filtered, dried, heated, or cooled before contacting with the room temperature nitrogen dioxide gas sensor.

In one embodiment, the room temperature nitrogen dioxide gas sensor may be housed in a casing designed for portability. In another embodiment, the room temperature nitrogen dioxide gas sensor may be housed in a casing for fixing or securing to a wall or to connect with a vessel or tubing. In one embodiment, the room temperature nitrogen dioxide gas sensor may be operated continually, similar to other emergency detectors (such as a smoke detector), and may have a set threshold of nitrogen dioxide gas concentration beyond which an audible and/or visible alarm is triggered.

In one embodiment, the method further comprises transmitting the response factor, wherein the room temperature nitrogen dioxide gas sensor further comprises a computing device configured to transmit a data measurement. The data may be transmitted by transferring to a wired or wireless network, as mentioned previously regarding the computing device. In another embodiment, the sensor may transmit only raw data, such as the resistivity reading across the electrodes. This raw data may be received by another computing device in the network, and then used to calculate the response factor, the concentration of nitrogen dioxide, a rate of change, or some other parameter. In another embodiment, raw data may be passed to another sensor, which appends the raw data with other data, and then sends to a computing device for processing. This sending and processing of data may be performed in an "Internet of Things" (IoT) strategy and includes embodiments using handheld devices, mobile apps, and remote monitoring.

In one embodiment, the method of using the room temperature nitrogen dioxide gas sensor further comprises a calibration process. For instance, gas samples comprising known concentrations of nitrogen dioxide may be brought into contact with the room temperature nitrogen dioxide gas sensor, and the corresponding response may be measured. A person having ordinary skill in the art would be able to construct a calibration curve or plot based on the measured response of the room temperature nitrogen dioxide gas sensor when in contact with the different known gas samples.

In one embodiment, a gas sample in contact with the room temperature nitrogen dioxide gas sensor includes nitrogen dioxide gas and at least one compound selected from the group consisting of $NH_3$, $H_2$, n-butane, $O_2$, $CO_2$, $N_2$, pentane, butene, and pentene, wherein a nitrogen dioxide selectivity of the nitrogen dioxide gas sensor is at least 70% by mole, preferably at least 80% by mole, more preferably at least 85% by mole. As used herein, the term "nitrogen dioxide selectivity" refers to a ratio of a number of moles of the nitrogen dioxide gas that are adsorbed onto the room temperature nitrogen dioxide gas sensor relative to the total number of moles of gas molecules that are adsorbed onto the room temperature nitrogen dioxide gas sensor. For example, a nitrogen dioxide selectivity of the 80% by mole refers to an embodiment wherein 80% of all species adsorbed onto the room temperature nitrogen dioxide gas sensor are nitrogen dioxide. The nitrogen dioxide selectivity may be related to the specific surface area and the concentration of oxygen vacancies of the room temperature nitrogen dioxide gas sensor.

In one embodiment, the decrease in the second resistivity and/or first resistivity has a response time of 30-180 s, preferably 35-120 s, more preferably 40-80 s. However, in some embodiments, the response time may be shorter than 30 s or longer than 180 s. As defined here, the response time is the time needed by the room temperature nitrogen dioxide gas sensor to attain 90% of its saturation state value (i.e., the saturation state value may be thought of as the maximum response for a specific gas sample). The recovery time is defined as the time required for the maximum response to return to this 90% saturation state value once the particular gas sample is removed or exchanged with a gas producing essentially no response signal. In one embodiment, the decrease in the first resistivity may have a recovery time of 200-400 s, preferably 250-380 s, more preferably 280-360 s. However, in some embodiments, the recovery time may be shorter than 200 s or longer than 400 s. Generally, in some embodiments, as the concentration of nitrogen dioxide in a gas sample increases, the recovery time increases and/or the response time decreases. However in some embodiments and/or certain concentration ranges, the concentration of nitrogen dioxide may increase while the response time and/or recovery time may be essentially unchanged. In alternative embodiments, the response time and/or the recovery time may be defined by the time it takes the response signal to reach a percentage lower than or greater than 90% of the saturation state value.

In one embodiment, the method has a repeatability of at least 99%, preferably, at least 99.5%, over a time period of at least one hour, preferably at least one month, more preferably, at least one year. In one embodiment, the method has a repeatability of at least 99%, preferably at least 99.5% for at least 4 separate instances of contacting with nitrogen dioxide gas, preferably at least 10 separate instances, more preferably at least 100 separate instances, even more preferably at least 1,000 separate instances. In other embodiments, the method may have a repeatability of at least 65%, at least 70%, at least 75%, at least 80%, at least 85%, at least 90% or at least 95% for any of the previously mentioned number of instances or time intervals. As defined here, repeatability refers to the percentage of a response, relative to the response of an initial measurement, for an identical gas sample or control being measured more than once. For instance, a room temperature nitrogen dioxide gas sensor may have an initial response of $5.0 \times 10^3$ MΩ for a gas sample of 15 ppm nitrogen dioxide gas in $N_2$. After numerous measurements, the same gas sample may then produce a response of $4.8 \times 10^3$ MΩ, which indicates a repeatability of $(0.2 \times 10^3)/(5.0 \times 10^3) \times 100\% = 96\%$.

In one embodiment, the method may further comprise a step of cleaning or recharging the room temperature nitrogen dioxide gas sensor. Here, the sensor may be heated above room temperature, for instance, to 80-120° C., 120-200° C., or 200-500° C. and/or may be contacted with one or more compounds such as a solvent or an acid, in order to remove impurities, though in other embodiments, the cleaning may involve exposure to light irradiation, such as with UV light.

In one embodiment, the cleaning or recharging may increase the repeatability of a room temperature nitrogen dioxide gas sensor.

The room temperature nitrogen dioxide gas sensor may further be utilized to detect and/or determine a concentration of other gaseous compounds that affect its electrical resistance upon adsorption. Exemplary gaseous compounds without limitations may include carbon monoxide, nitrogen monoxide, hydrogen, methane, ethane, methanol, ethanol, hydrogen sulfide, etc. In view of that, the room temperature nitrogen dioxide gas sensor may also be used to detect exhaust gases or toxic gases, for example, in automobile industries and/or in air pollution control systems.

In an alternative embodiment, a room temperature nitrogen dioxide gas sensor may be used in the field of batteries, fuel cells, photo-chemical cells, heated hydrogen sensors, heated nitrogen dioxide sensors, semiconductors (such as field effect transistors), magnetic semiconductors, capacitors, data storage devices, biosensors (such as redox protein sensors), photovoltaics, liquid crystal screens, plasma screens, touch screens, OLEDs, antistatic deposits, optical coatings, reflective coverings, anti-reflection coatings, and/or reaction catalysis. Similarly, in one embodiment, the room temperature nitrogen dioxide gas sensor, having a gold nanostructure, may be used to detect nitrogen dioxide or some other analyte using surface enhanced Raman spectroscopy (SERS).

In one embodiment, two or more separate substrates having electrodes with $SnO_2$ layers and gold nanoparticles may be connected in series and/or parallel in order to create an array of room temperature nitrogen dioxide gas sensors.

The examples below are intended to further illustrate protocols for preparing, characterizing the room temperature nitrogen dioxide gas sensor, and uses thereof, and are not intended to limit the scope of the claims. In the examples, "sample" and "sensor" may be used interchangeably to describe the room temperature nitrogen dioxide gas sensor. See Q. A. Drmosh, Z. H. Yamani, A. K. Mohamedkhair, A. H. Y. Hendi, M. K. Hossain, and Ahmed Ibrahim, "Gold nanoparticles incorporated $SnO_2$ thin film: highly responsive and selective detection of $NO_2$ at room temperature," *Materials Letters*. 214, 283-286 (2018)—incorporated herein by reference in its entirety.

Example 1

Fabricating the Sensor

The $SnO_2$ and metallic Au films were fabricated using RF/DC sputtering (NSC4000-Nanomaster). The base pressure of the sputter chamber prior to deposition was $3.1\times10^{-6}$ Torr, and the working pressure was maintained at $3.5\times10^{-3}$ Torr with the introduction of Ar gas (>99.99% Ar). Before the deposition, the substrates used in this work were cleaned by the several sequential steps of ultra-sonication in acetone, then isopropanol, and finally deionized water. The duration of each sonication step was 25 min, and afterwards, the samples were dried by a dry $N_2$ stream.

The fabrication of the sensor was carried out in three steps: (1) fabrication of $SnO_2$ thin films using RF sputtering; (2) preparation of Au layer onto the surface of the $SnO_2$ film using DC sputtering; and (3) conversion of Au layer to different nanostructured Au morphologies. For the fabrication of $SnO_2$ thin films, the deposition power was set at 250 W and a deposition time of 90 min was used. For the fabrication of Au thin films, the deposition power was set at 30 W and the deposition time of 45 s was used. An annealing step at 600° C. in argon or air (ramping rate: 15° C./min) for 1 h was also performed to achieve highly dispersed nanostructured Au on $SnO_2$ film. The fabricated samples were characterized by X-ray diffraction (XRD), field emission scanning electron microscopy (FESEM), atomic force microscopy (AFM), X-ray photoelectron spectroscopy (XPS), and double beam UV/Vis spectrophotometry.

Example 2

Sensor Characterization

The sensing characteristics of the fabricated sensors towards $NO_2$ were studied using the sequential introduction of air and $NO_2$-balanced nitrogen into the test chamber. A Linkam stage (Model HFS-600E-PB4, UK) was used as the test chamber and enabled temperature control up to 600° C. with a stability of less than 0.1° C. $NO_2$ gas was mixed with the diluting air using two mass flow controllers (MFCs) connected with an external X PH-100 power hub supply. Before each test, the Linkam stage was purged by dried air with a flow rate of 40 sccm (standard cubic centimeter per minute, or $cm^3$/min). The gas sensing response was evaluated by the normalized resistance change as given by the equation:

$$\text{Response (\%)} = \frac{R_0 - R_g}{R_g} \times 100\%$$

where $R_0$ and $R_g$ are the resistances of the sensor in air and analyte gas, respectively. These resistances of the sensor were determined with an Agilent B1500A Semiconductor Device Analyzer (SDA). The sensor response was investigated with 600 ppb-50 ppm concentrations of $NO_2$ gas in dry air over a temperature range of RT (room temperature) to 500° C. The sensing performance of the fabricated materials was systematically evaluated by studying three important sensing characteristics: (I) response to $NO_2$ gas, (II) response time, and (III) selectivity.

Example 3

Morphological Analysis of the Thin Film Layer

Figure 1B:
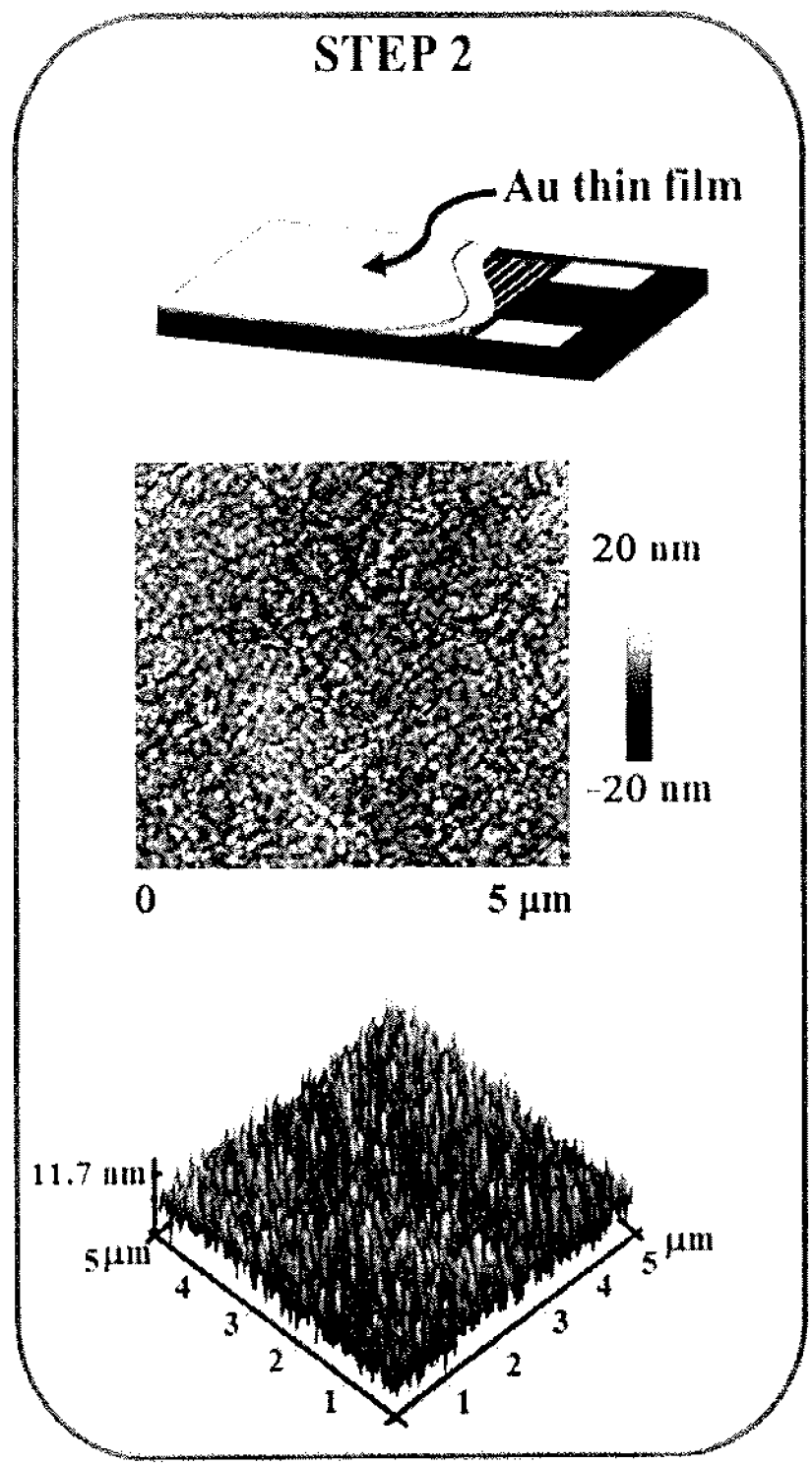
FIG. 1B shows a schematic of a Au—$SnO_2$ layer with 2D and 3D AFM images.
Figure 1C:
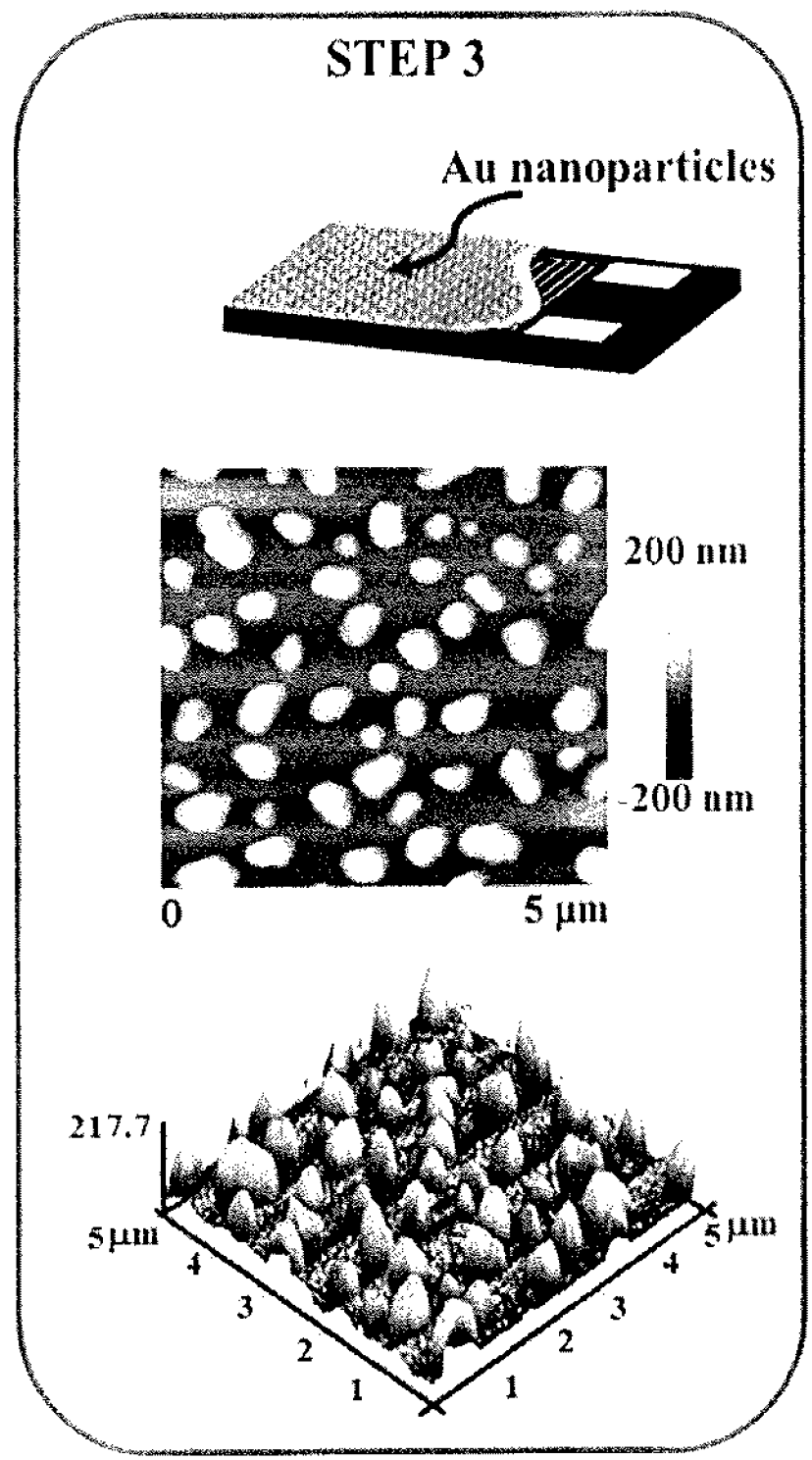
FIG. 1C shows a schematic of a Au nanoparticle-loaded $SnO_2$ layer with 2D and 3D AFM images.
Figure 2A:
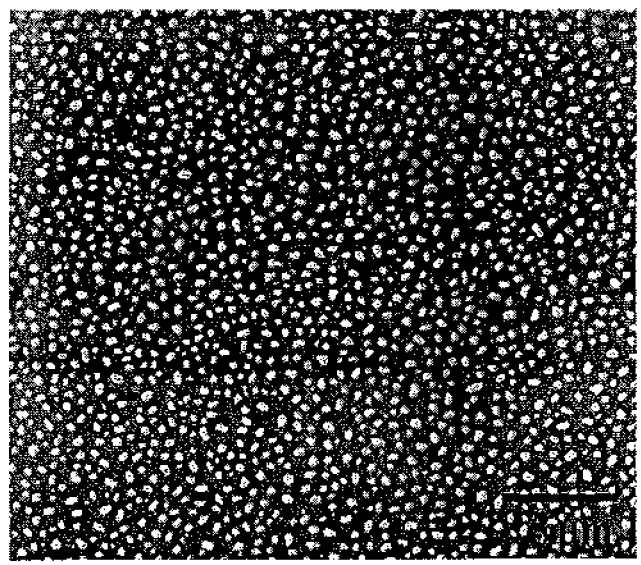
FIG. 2A is an FESEM image of a Au nanoparticle-loaded $SnO_2$ layer.
Figure 2B:
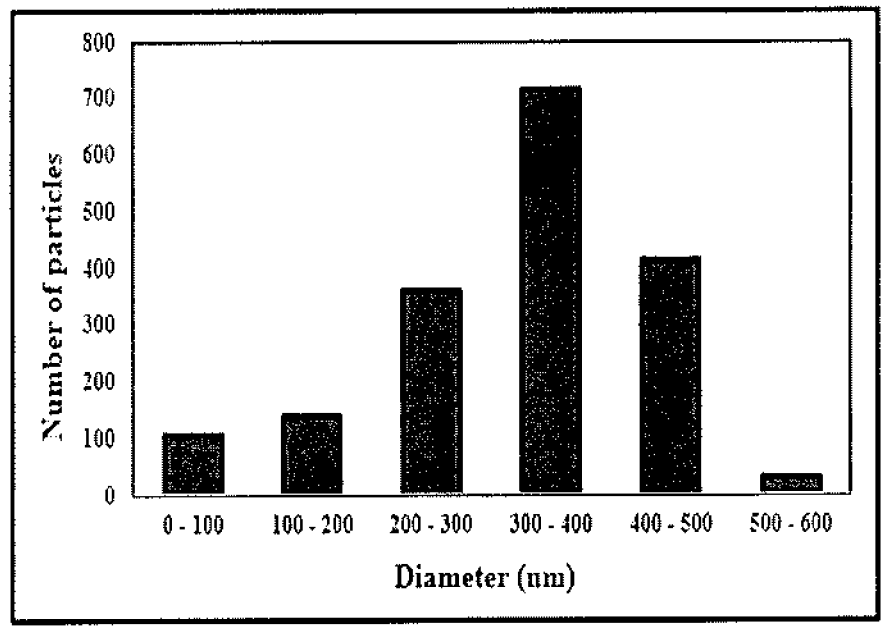
FIG. 2B is a particle size distribution of the Au nanoparticles of a Au nanoparticle-loaded $SnO_2$ layer.
Figure 3A:
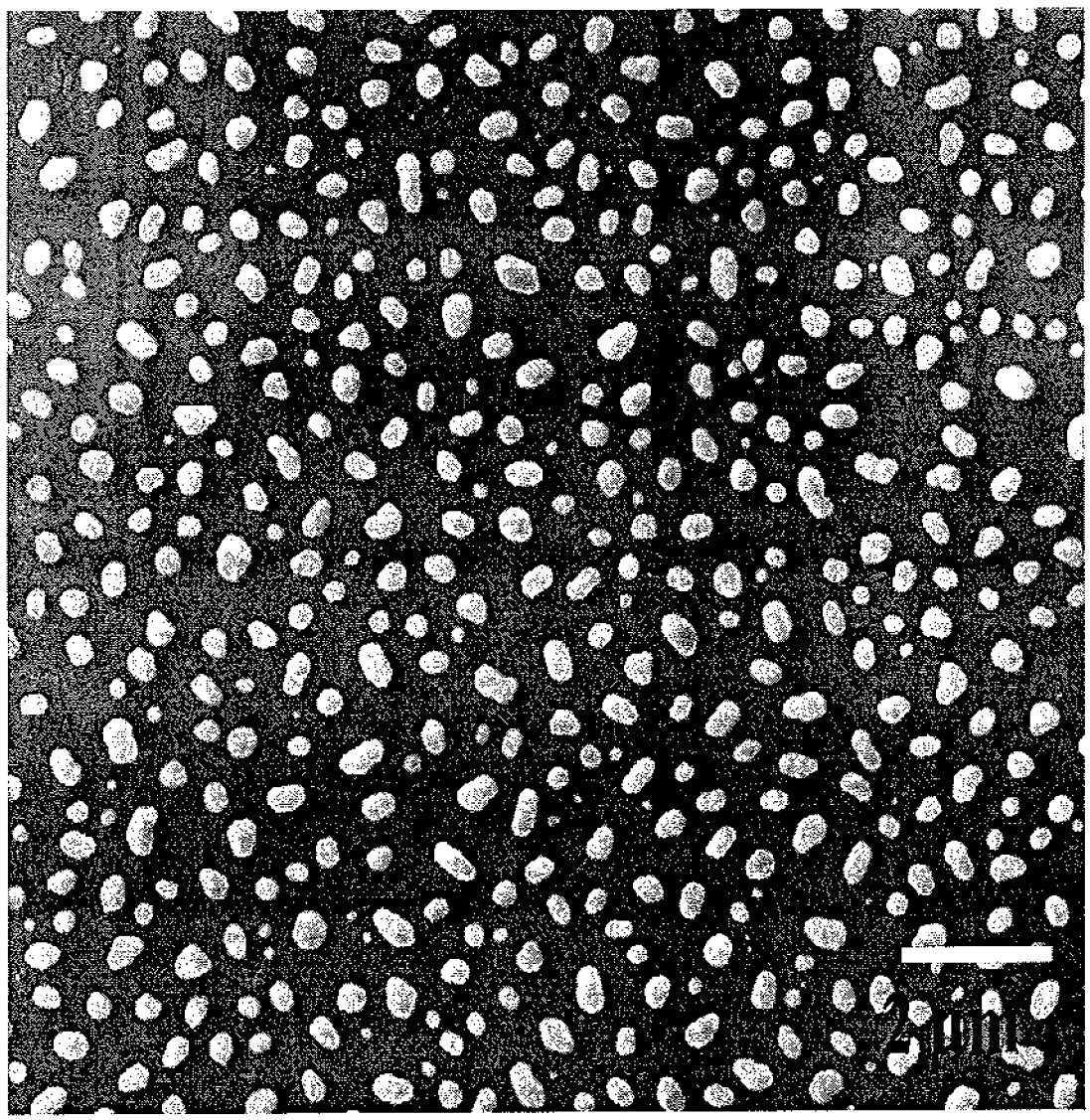
FIG. 3A is a highly-magnified FESEM image of a Au nanoparticle-loaded $SnO_2$ layer, with a scale bar of 2 μm.
Figure 3B:
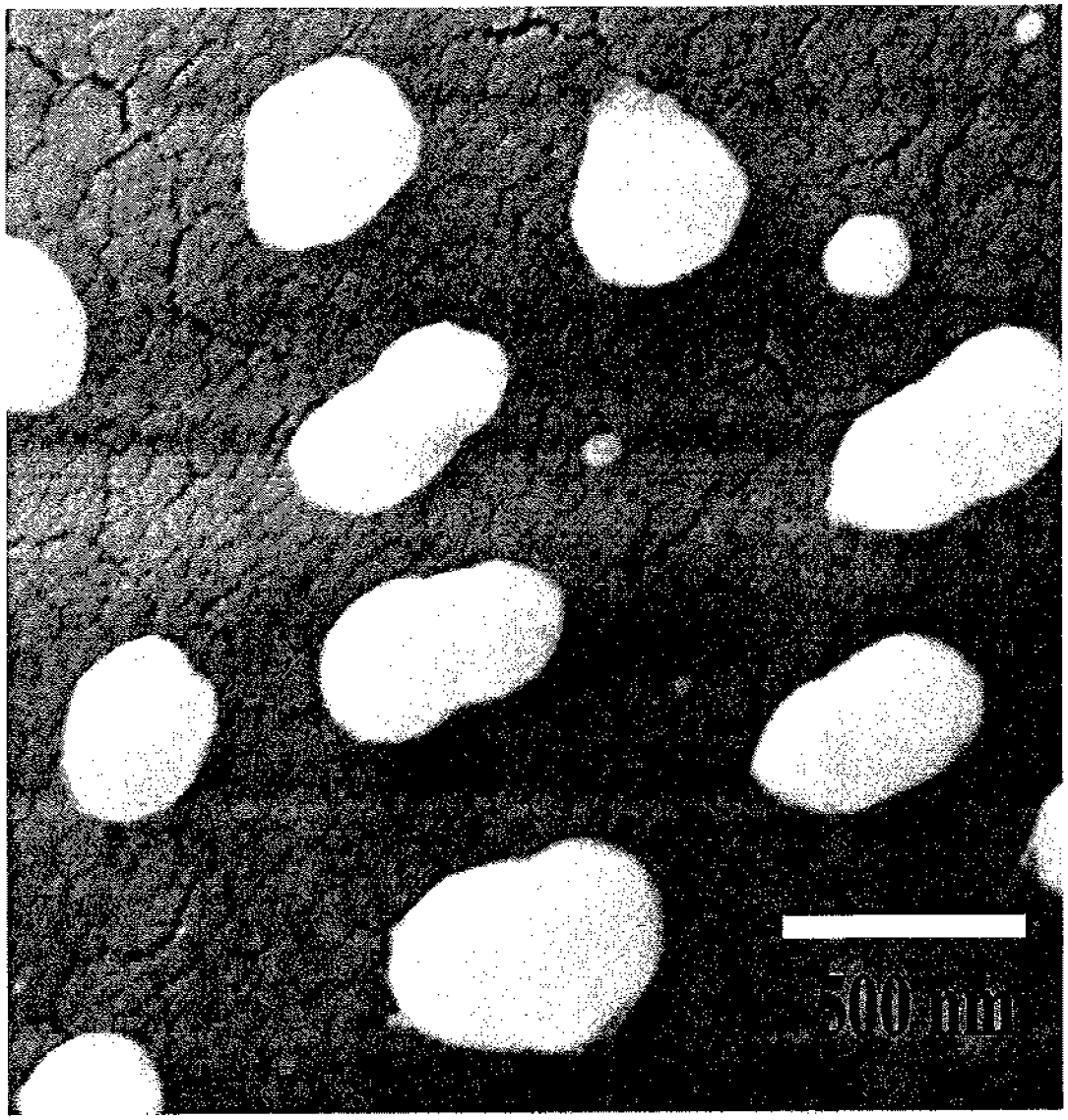
FIG. 3B is another highly-magnified FESEM image of a Au nanoparticle-loaded $SnO_2$ layer, with a scale bar of 200 nm.
Figure 3C:
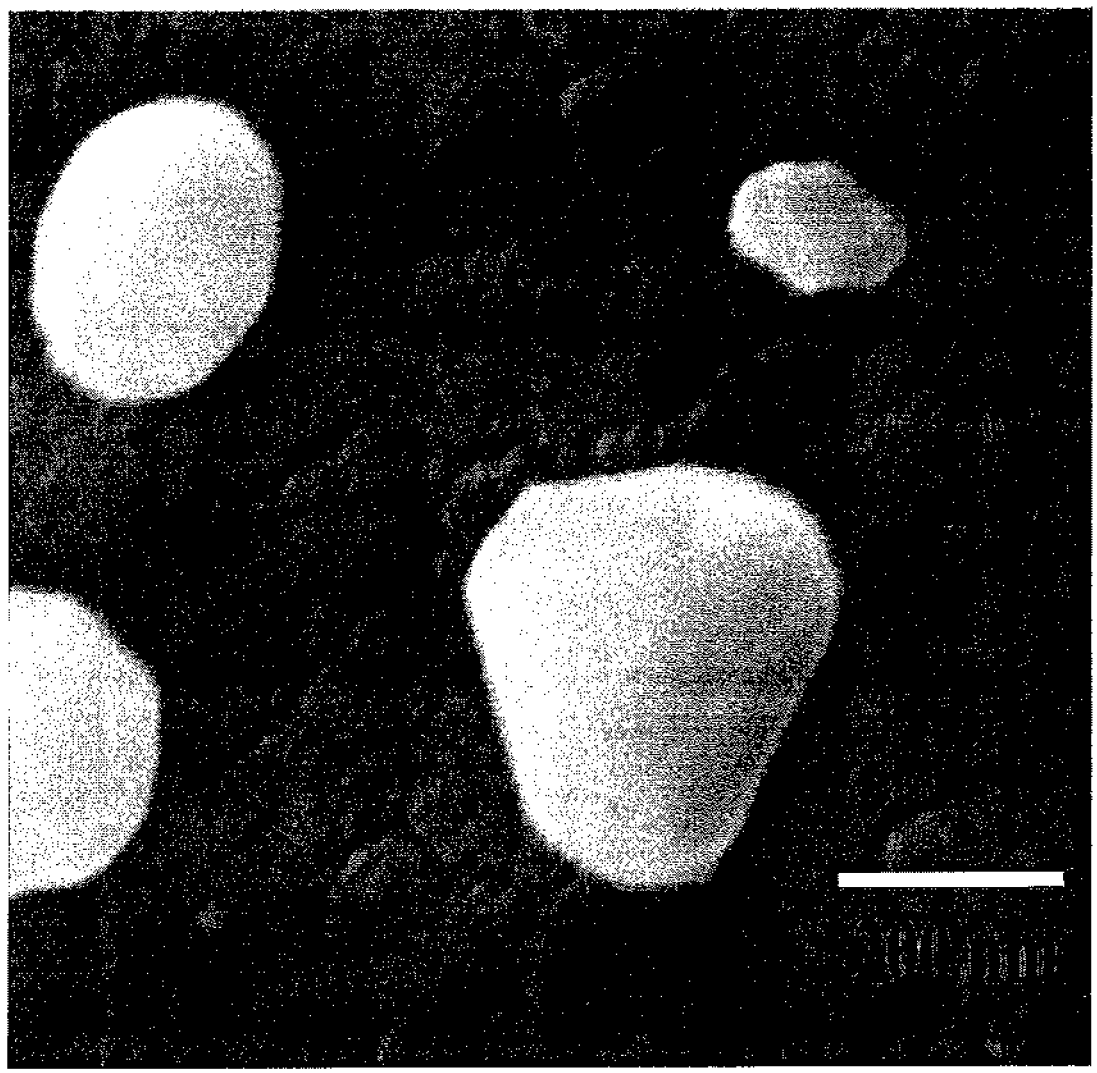
FIG. 3C is another highly-magnified FESEM image of a Au nanoparticle-loaded $SnO_2$ layer, with a scale bar of 500 nm.
Figure 3D:
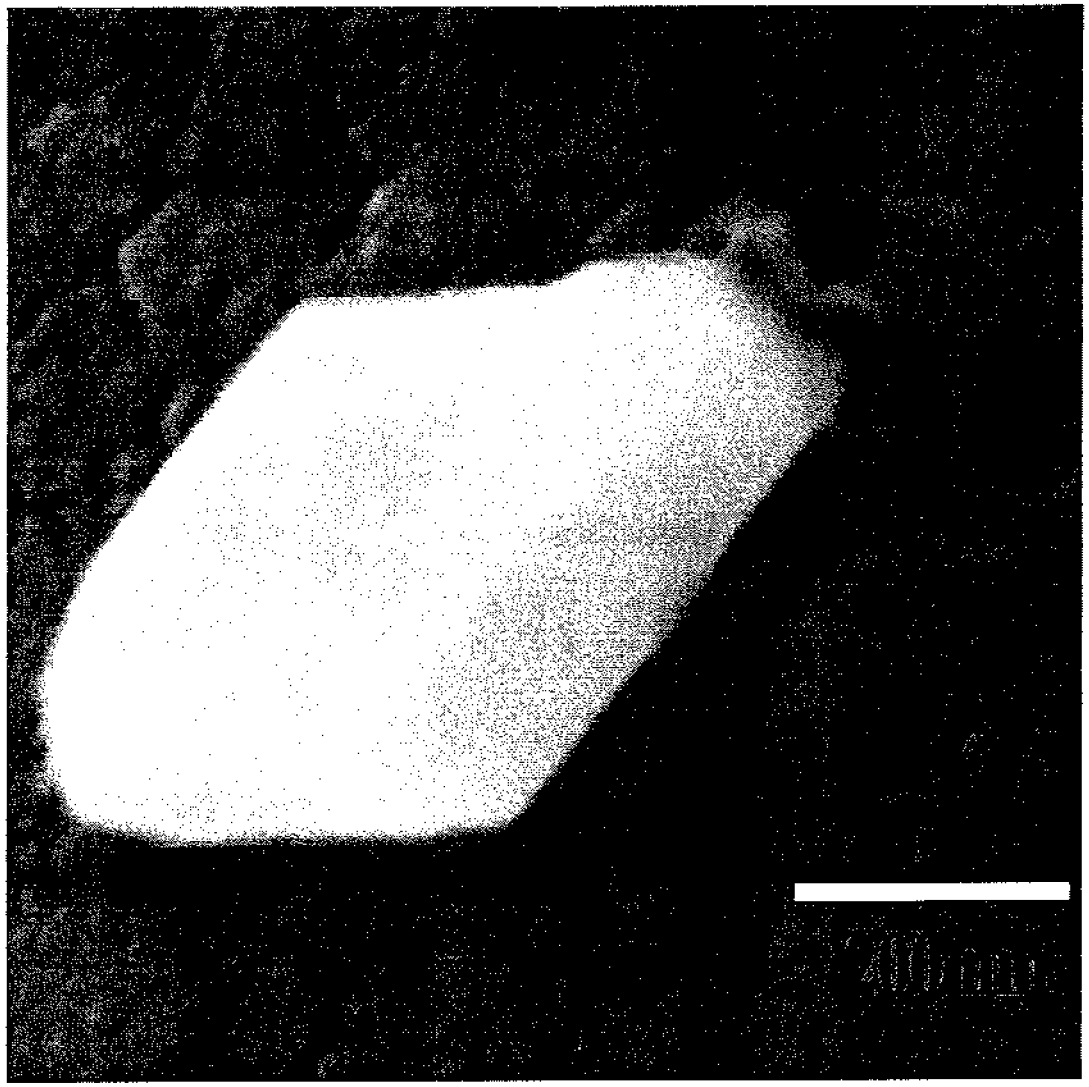
FIG. 3D is another highly-magnified FESEM image of a Au nanoparticle-loaded $SnO_2$ layer, with a scale bar of 500 nm.

FIGS. 1A-1C exhibits schematic, two-dimensional (2D), and three-dimensional (3D) AFM images of the pristine $SnO_2$ films (i.e., $SnO_2$ films having no gold layer) (FIG. 1A), $SnO_2$ films loaded with an Au layer (FIG. 1B), and $SnO_2$ films loaded with Au nanoparticles (FIG. 1C). The 2D and 3D AFM images show a uniform distribution of fine particles in the pristine $SnO_2$, and $SnO_2$ films loaded with an Au layer (FIGS. 1A and 1B) while clear dispersion of Au nanoparticles can be visualized in the S3 film (FIG. 1C). FESEM (field emission scanning electron microscopy) images of the Au nanoparticles loaded $SnO_2$ film (FIG. 2A) display the uniform distribution of Au nanoparticles over the $SnO_2$ film surface. The histogram of size distribution of the obtained Au nanoparticles in the Au nanoparticle-decorated $SnO_2$ sample is shown in FIG. 2B, revealing an average particle size of 350 nm. To elucidate the morphology of the fabricated films, highly magnified FESEM images of Au nanoparticle-loaded $SnO_2$ film were obtained as displayed in FIGS. 3A-3D. FESEM observations demonstrate the multiple facets and plate-like shapes of the obtained Au nanoparticles. This morphology is preferable for gas sensing applications due the increased number of oxygen adsorption sites.

Figures 4A, 4B:
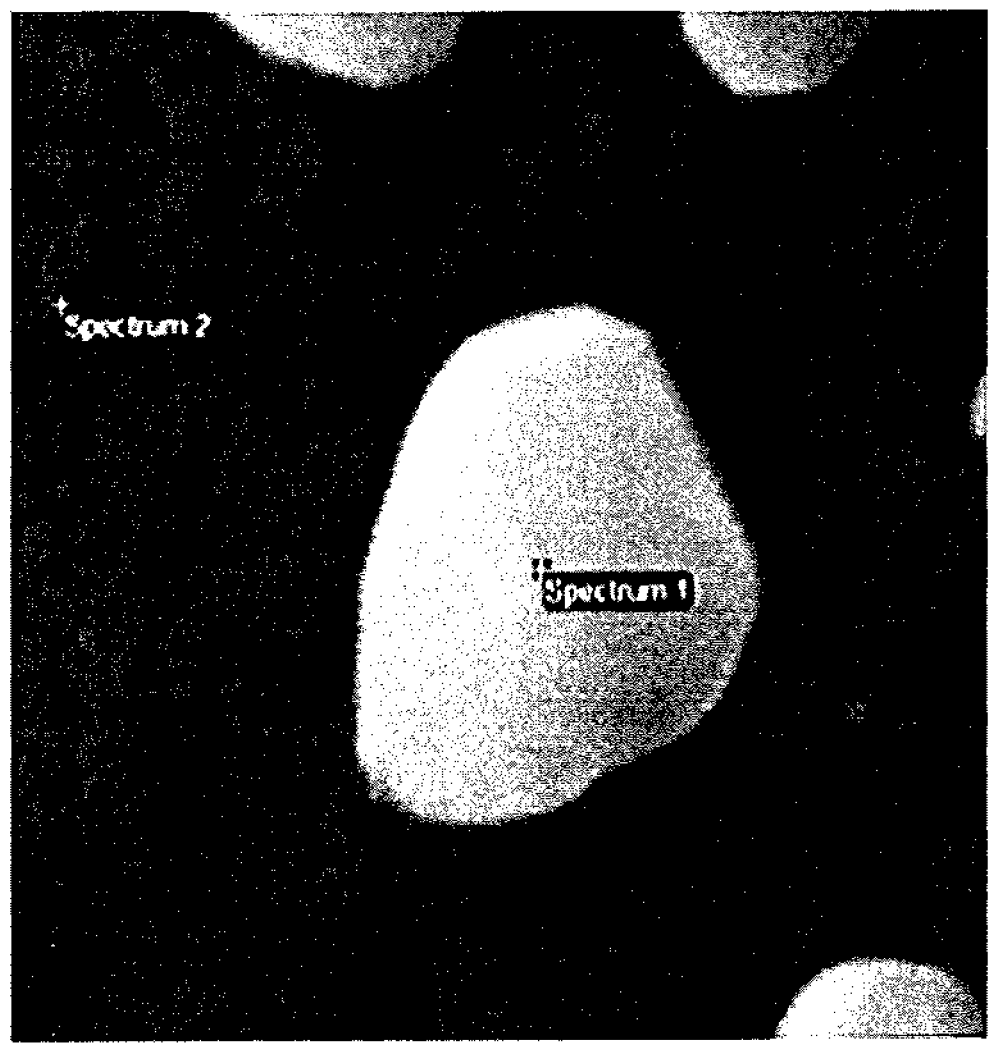
FIG. 4A is a table showing an elemental EDX analysis of a single Au nanoparticle on an $SnO_2$ film.
FIG. 4B is an image of a single Au nanoparticle on a $SnO_2$ film sampled for the EDX analysis in FIG. 4A.
Figure 5A:
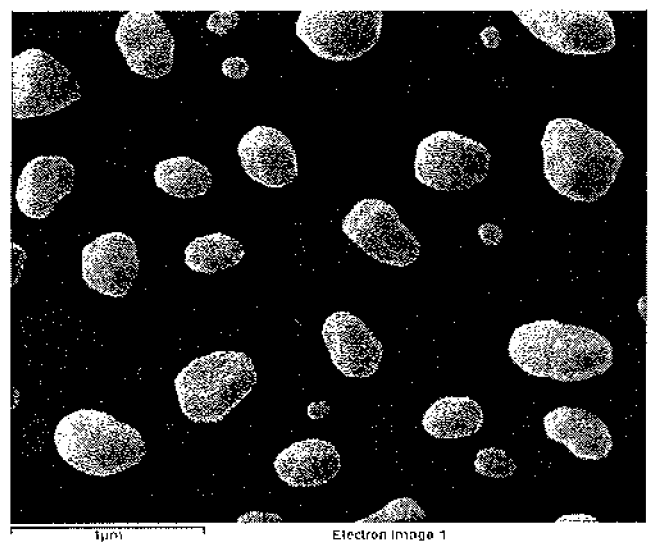
FIG. 5A is an FESEM image of a Au nanoparticle-loaded $SnO_2$ layer.
Figure 5B:
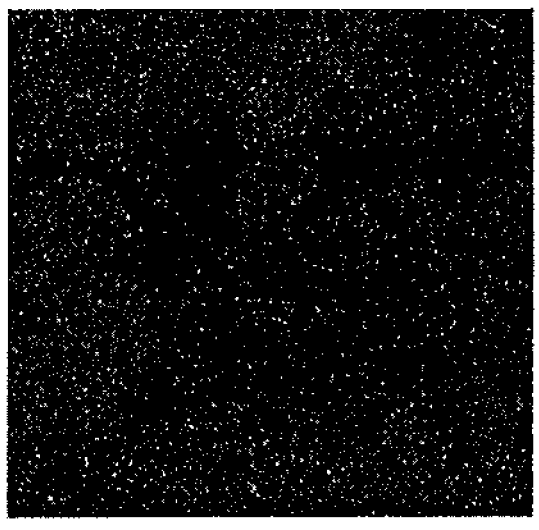
FIG. 5B is an EDS micrograph of the FESEM image in FIG. 5A, showing the Sn signal.
Figure 5C:
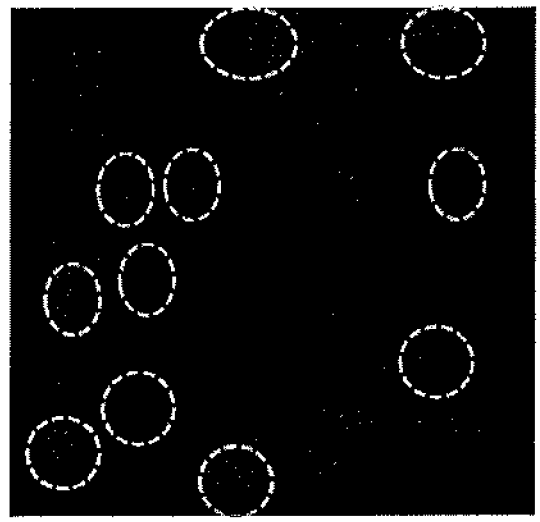
FIG. 5C is an EDS micrograph of the FESEM image in FIG. 5A, showing the Au signal.

To further elucidate the uniform distribution of Au nanoparticles on the $SnO_2$ film surface, a high-resolution FESEM-EDX image of Au nanoparticles loaded $SnO_2$ thin film was obtained (FIG. 4B). In order to investigate the Au distribution on the surface of $SnO_2$ film, and to answer the question of whether the Au layer was completely converted to Au nanoparticles, EDX analysis and EDX mapping were performed. The EDX point spectra (FIG. 4B) taken at the surface of the $SnO_2$ film and the single Au nanoparticle indicate the presence of both Au and Sn. FIG. 4A shows the atomic percentage composition of sample elements (O, Sn, and Au) detected through the above-mentioned spectra. The data recorded from spectrum 1 indicate the excess of Au nanoparticles in this site compared to Sn and O. However, spectrum 2 shows the predominance of Sn and O with some tiny Au nanoparticles. The presence of these tiny particles on the $SnO_2$ surface in addition to the agglomerated Au particles was confirmed by EDX mapping as shown in FIGS. 5A-5C. This is an interesting finding since both types of Au nanoparticles may contribute to enhance the performance of this sensor.

Example 4

Structural Analysis of the Thin Film Layer

Figure 6:
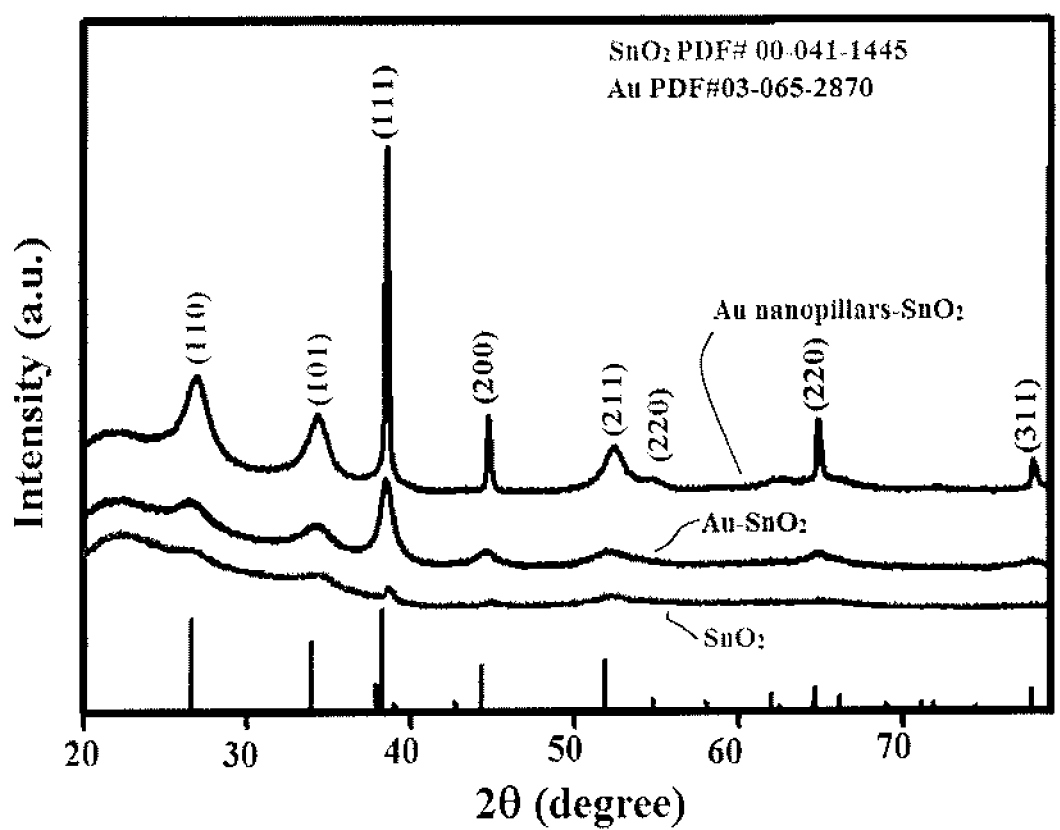
FIG. 6 shows XRD patterns of $SnO_2$, Au—$SnO_2$, and Au nanoparticle-loaded $SnO_2$ film.

FIG. 6 shows XRD patterns of the $SnO_2$ films, Au layer loaded $SnO_2$ films and Au nanoparticles loaded $SnO_2$ films. The $SnO_2$ film and the Au layer loaded $SnO_2$ film exhibited low levels of crystallinity along the (110), (101), (200) and (211) planes of the tetragonal rutile structure of $SnO_2$ [B. Wang, et al., "Fabrication of a $SnO_2$ Nanowire Gas Sensor and Sensor Performance for Hydrogen," *J Phys. Chem. C,* 112 (2008) 6643-6647—incorporated herein by reference in its entirety]. Subsequently, the heat treatment of Au layer loaded $SnO_2$ film at the annealing temperature of 600° C. led to a significant improvement in the intensities of the diffraction peaks in the Au nanoparticles loaded $SnO_2$ film.

Example 5

Optical Analysis of the Thin Film Layer

Figure 7:
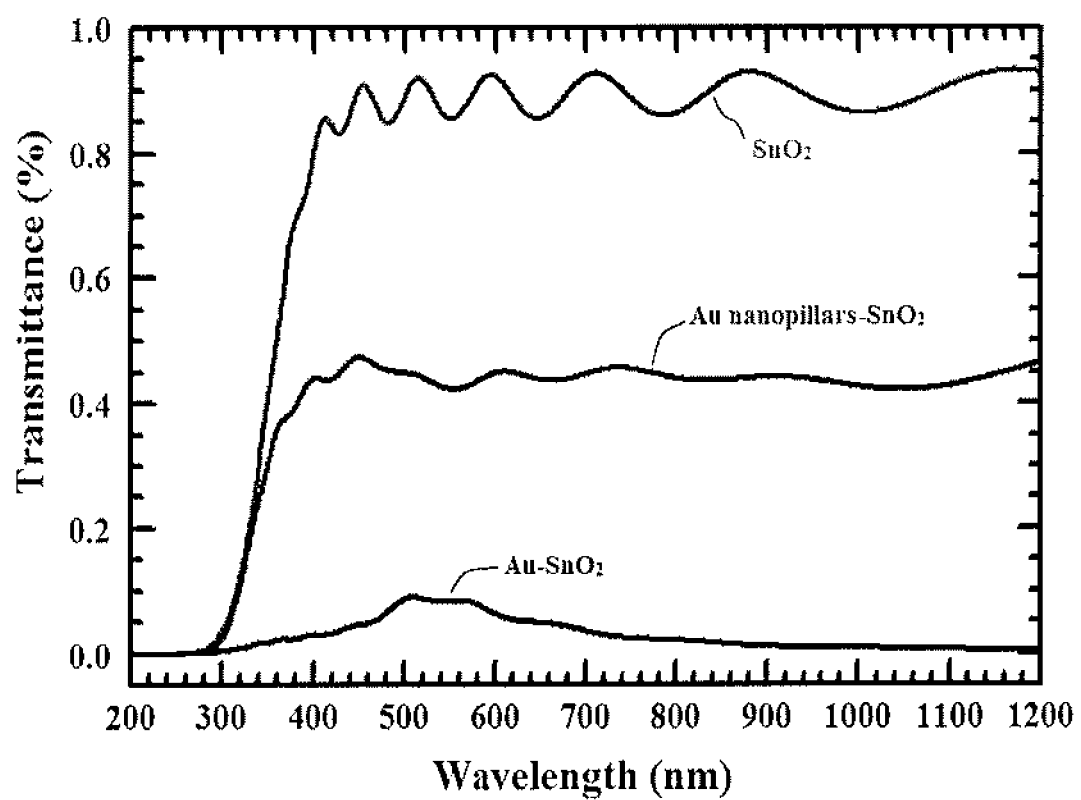
FIG. 7 shows UV/Vis transmittance spectra of $SnO_2$, Au—$SnO_2$ and Au nanoparticle-loaded $SnO_2$ film in the wavelength range of 200-1200 nm.

The optical transmittance of the obtained films is shown in FIG. 7. For the Si film, the transmittance is high. However, loading Au on the surface of $SnO_2$ film led to a significant drop in the optical transparency of the $SnO_2$ films, switching them from transparent to opaque. Subsequently, the transmittance of the Au layer loaded $SnO_2$ film was enhanced after heat treatment.

Example 6

Compositional Analysis of the Thin Film Layer

Figure 8A:
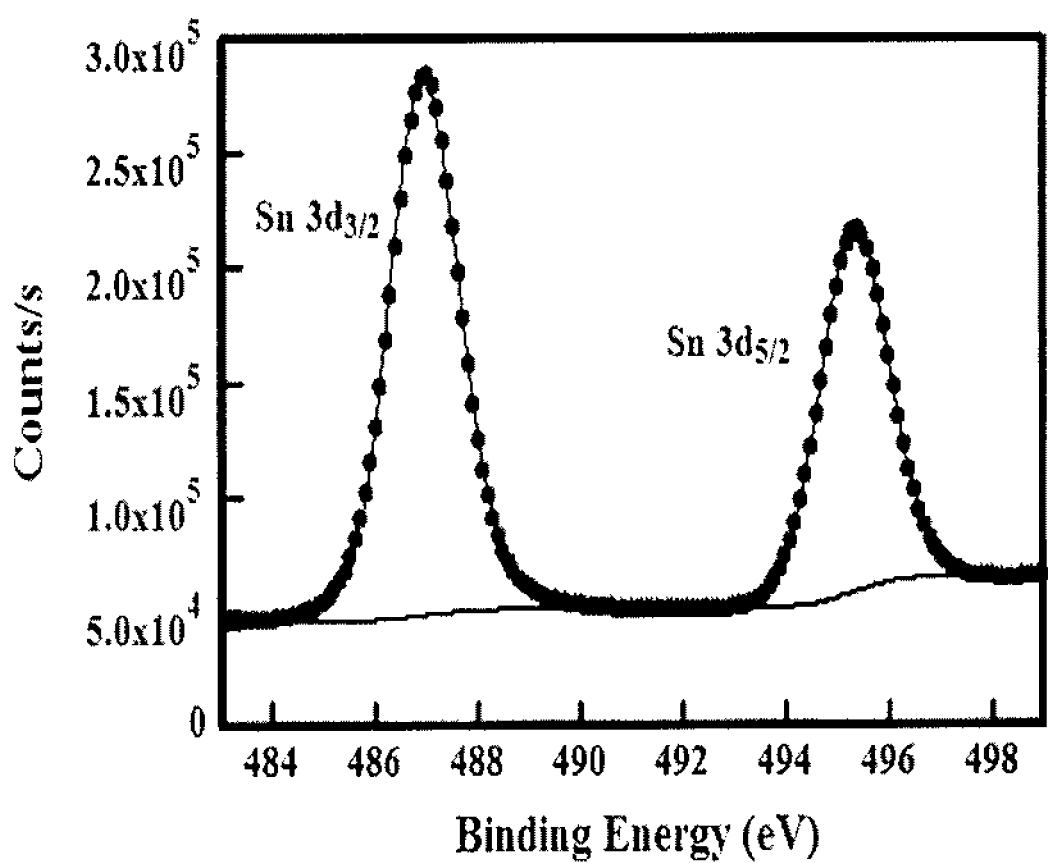
FIG. 8A shows an XPS core level spectra of Au nanoparticle-loaded $SnO_2$ film showing binding energy of Sn 3d electrons.
Figure 8B:
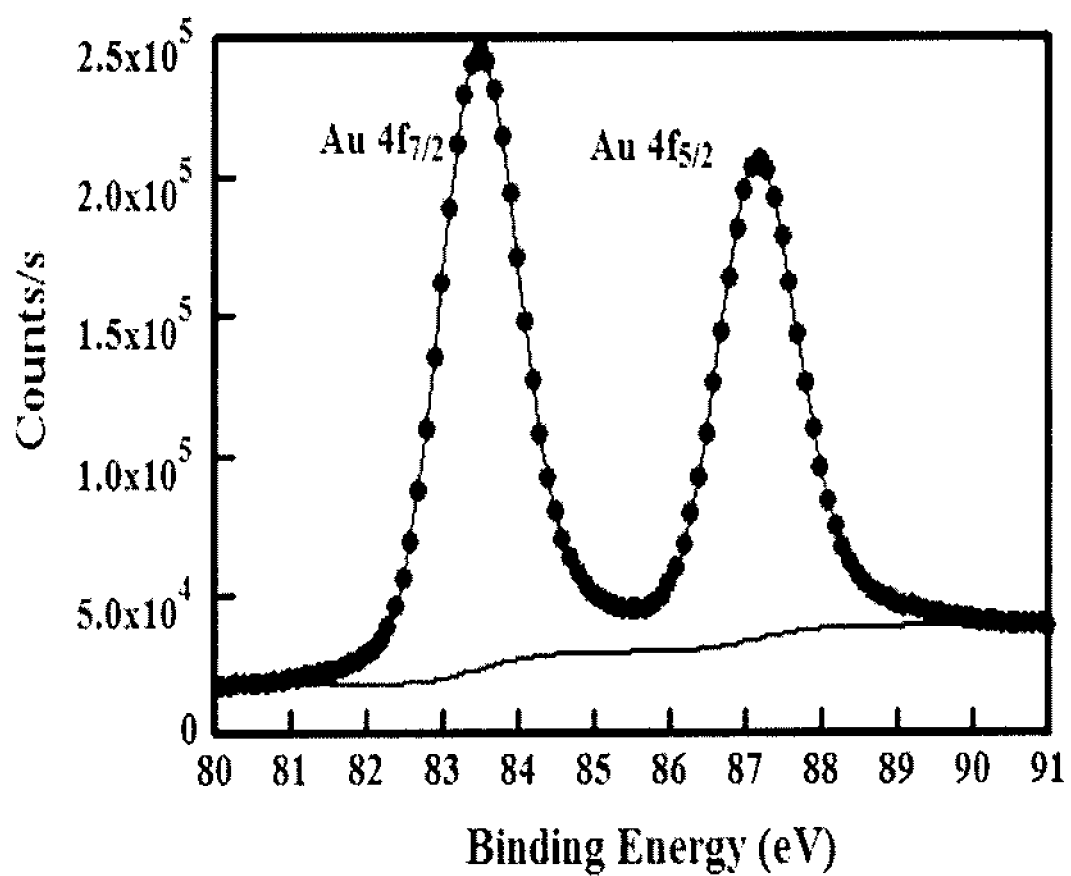
FIG. 8B shows an XPS core level spectra of Au nanoparticle-loaded $SnO_2$ film showing binding energy of Au 4f electrons.

FIG. 8 shows the XPS spectra of the S3 film. The Sn3d spectrum (FIG. 8A) was deconvoluted into two peaks positioned at binding energies of 486.9 eV and 495.3 eV, corresponding to the $Sn3d_{5/2}$ and $Sn3d_{3/2}$ levels, respectively. These values match those of Sn in the $Sn^{4+}$ oxidation state [Q. Ni, et al, "Characterization of the Mixed Oxide Layer Structure of the $Ti/SnO_2$—$Sb_2O_5$ Anode by Photoelectron Spectroscopy and Impedance Spectroscopy," *J. Electrochem. Soc.* 162 (2015) H40-H46—incorporated herein by reference in its entirety]. Similarly, the Au4f spectrum (FIG. 8B) was resolved into two peaks corresponding to $Au4f_{7/2}$ and $Au4f_{5/2}$, centered at binding energies of 83.6 eV and 87.2 eV, respectively, and together corresponding to $Au^0$ oxidation state [Y. Wu, et al, "The shape evolution of gold seeds and gold@silver core-shell nanostructures," *Nanotechnology* 20 (2009) 305602 (10 pp)—incorporated herein by reference in its entirety].

Example 7

Gas Sensing Properties

Figure 9:
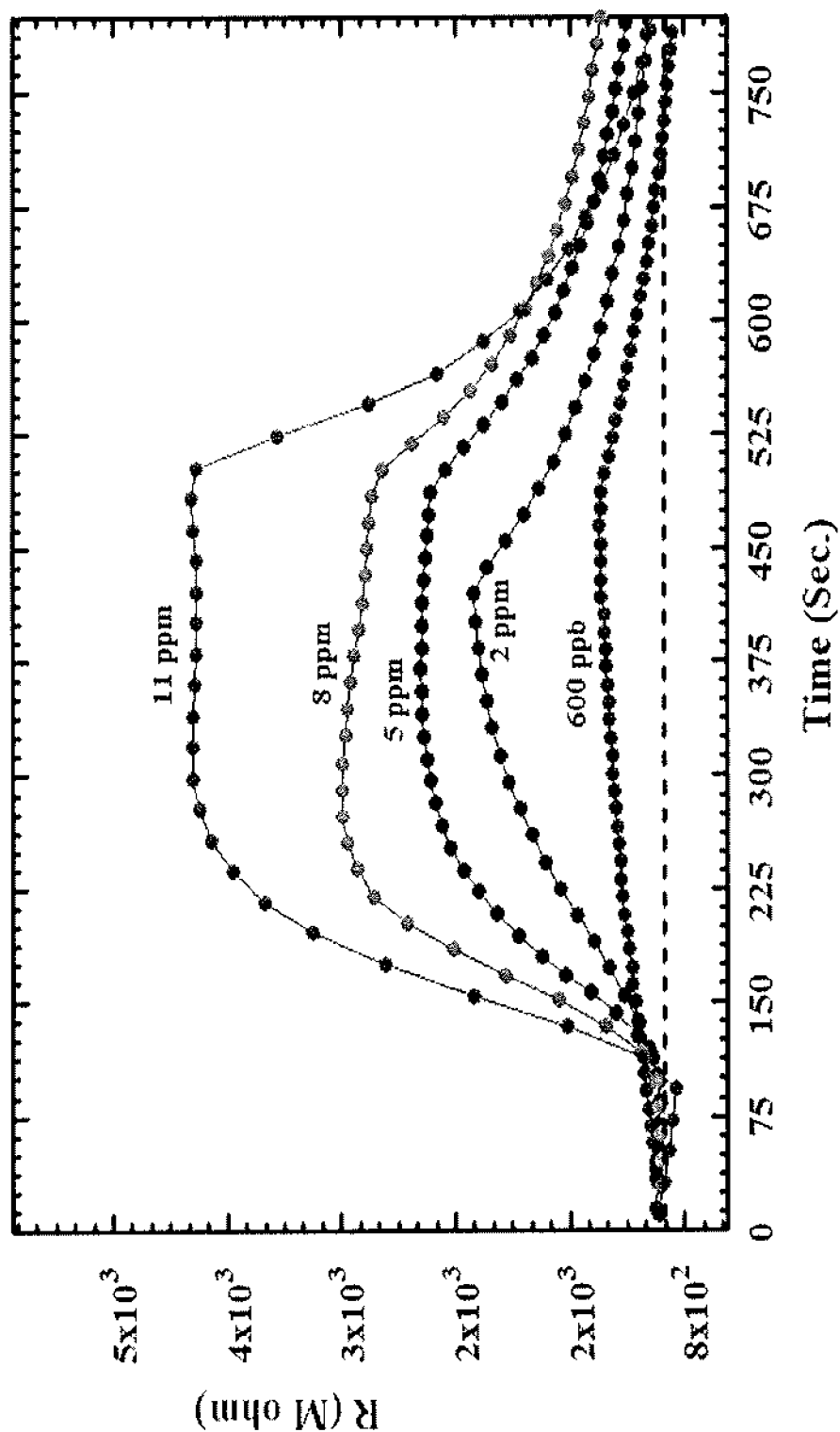
FIG. 9 shows a dynamic response of the room temperature nitrogen dioxide gas sensor for 600 ppb-11 ppm of $NO_2$ at room temperature.

The gas sensing performance (response, selectivity, response time) of the fabricated sensor was investigated at various concentrations of $NO_2$ and at different operating temperatures ranging from RT to 500° C. FIG. 9 displays the dynamic response curves of Au nanoparticles-loaded $SnO_2$ films as a function of time when the sensor is in contact with 600 ppb, 2 ppm, 5 ppm, 8 ppm, and 11 ppm $NO_2$ at RT.

As can be observed, the resistance values of the as fabricated sensors rapidly increase to high values when low concentrations of $NO_2$ (600 ppb to 11 ppm) are introduced into the chamber. Upon exposing the fabricated sensors to air, the sensors' resistance recovers to their initial values, which indicates the complete recovery of the sensor upon removal of $NO_2$.

Figure 10:
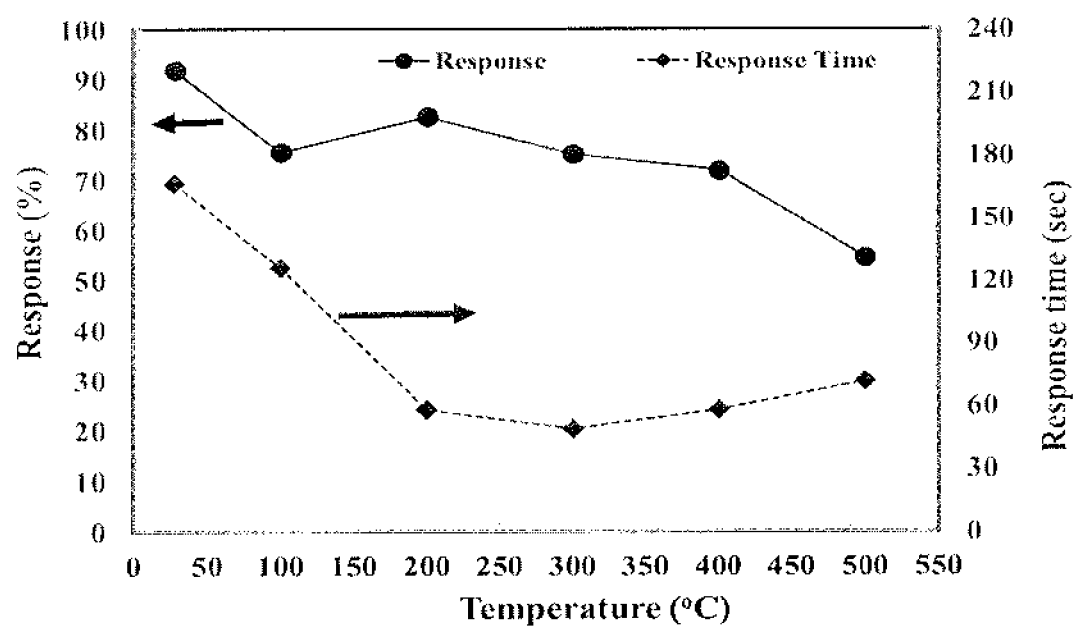
FIG. 10 shows the response (%) and response time (s) of the room temperature nitrogen dioxide gas sensor to 50 ppm $NO_2$ at different working temperatures.

The influence of operating temperature on the response and response time was studied for 50 ppm $NO_2$ with temperatures ranging from RT to 500° C., with the results shown in FIG. 10. As can be observed, the Au nanoparticles loaded $SnO_2$ sensor displayed a low response to $NO_2$ with an increase of temperature. This behavior indicates that the gas sensor detects $NO_2$ most effectively at RT. Response time is defined as the time required by the sensor to attain 90% of its saturation state value. FIG. 10 demonstrated that the response time of the fabricated sensor was about 70 s at RT, and that the response time decreases with increasing operating temperature.

Figure 11:
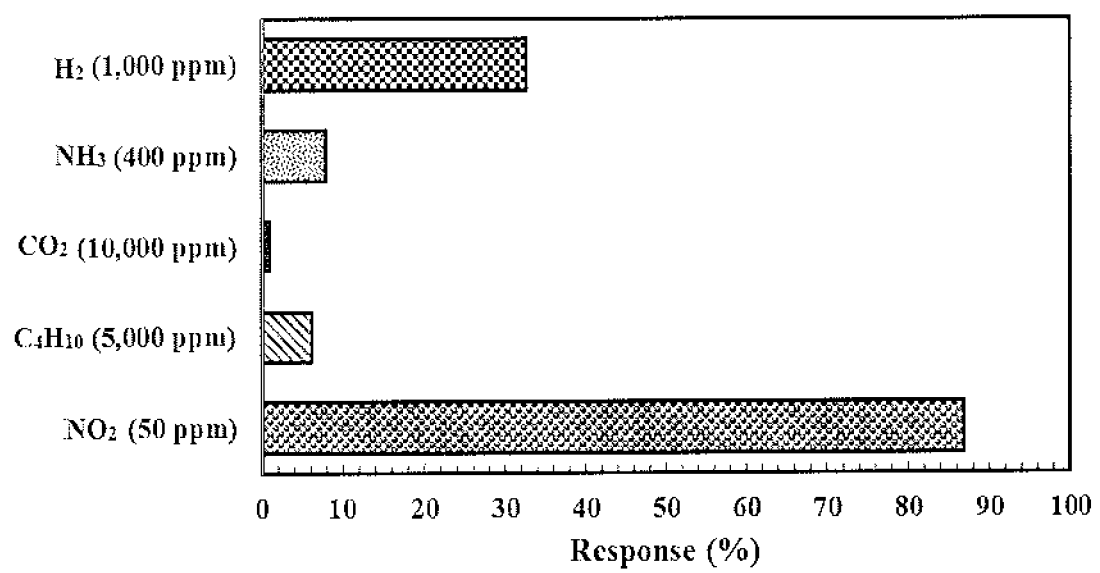
FIG. 11 shows the selectivity of the room temperature nitrogen dioxide gas sensor towards different gases at room temperature.

Selectivity, which is the ability of the sensor device to detect a certain gas among other gases, is considering as an important parameter for the development of gas sensors for nearly any desired application. To examine the selectivity of the fabricated sensors towards $NO_2$, we compared the response of our sensor in contact with 50 ppm $NO_2$ at RT with other gases at much higher concentration (FIG. 11). It is apparent that the Au nanoparticles incorporated $SnO_2$ sensor is almost insensitive toward $CO_2$, $NH_3$, and $C_4H_{10}$ while there is little response for 1000 ppm $H_2$, which is still much lower compared to 50 ppm $NO_2$.

Figure 12:
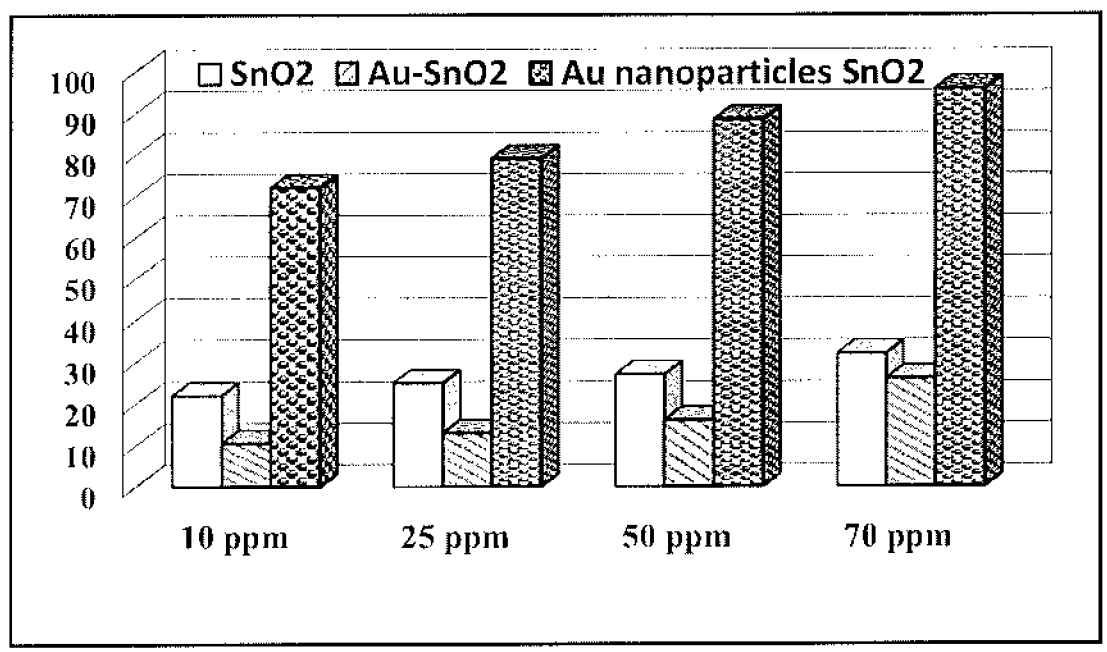
FIG. 12. Shows a comparison of the gas concentration-dependent response at RT for the $SnO_2$ layer, the Au—$SnO_2$ layer, and the room temperature nitrogen dioxide gas sensor.

The RT response of the three prepared sensors ($SnO_2$, Au—$SnO_2$, and Au nanoparticles $SnO_2$) to $NO_2$ (at concentrations of 10, 25, 50, and 75 ppm) is displayed in FIG. 12. As can be seen, the Au nanoparticles $SnO_2$ sensor showed excellent response at RT higher than other sensors, and its response increased with $NO_2$ concentrations.

Figure 13A:
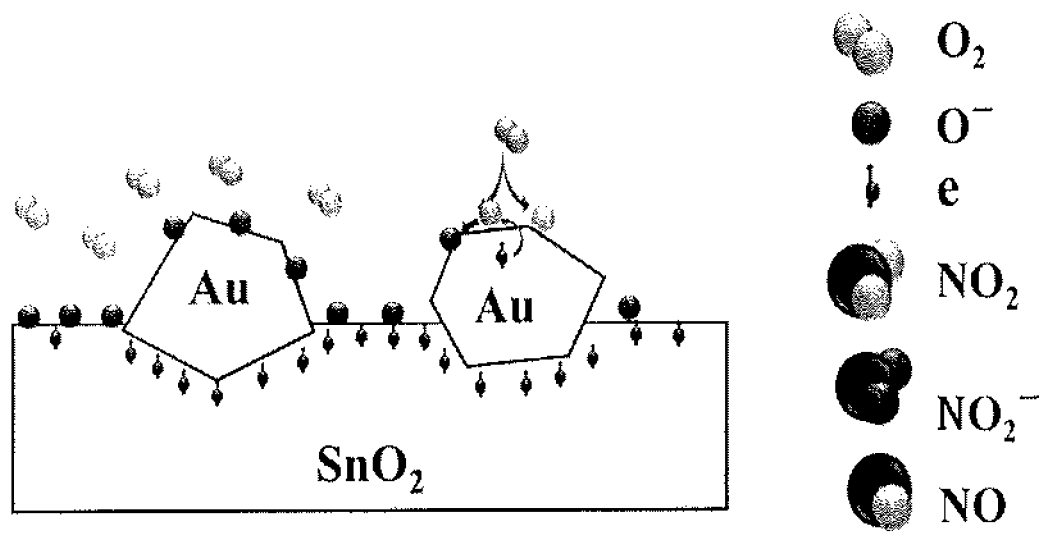
FIG. 13A shows a first step in a proposed sensing mechanism of the Au nanoparticle-loaded $SnO_2$ film for detecting $NO_2$ gas.
Figure 13B:
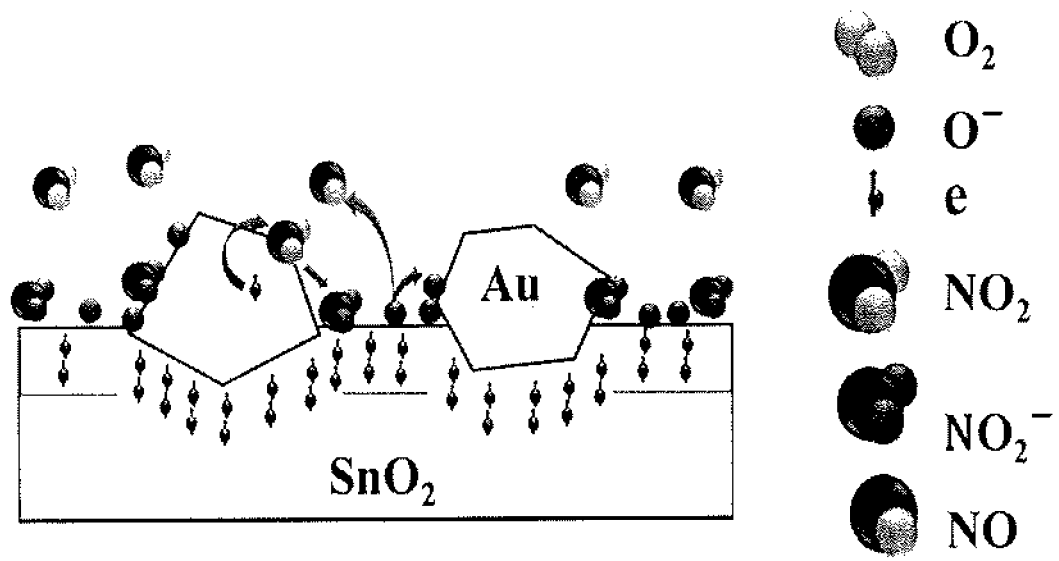
FIG. 13B shows a second step in a proposed sensing mechanism of the Au nanoparticle-loaded $SnO_2$ film for detecting $NO_2$ gas.

The high sensitivity and selectivity of the fabricated sensor at RT may be a result of the excellent dispersion of Au-nanoparticles loaded on the surfaces of $SnO_2$ films, which facilitates the ion adsorption of oxygen species ($O^{2-}$, $O^-$, $O_2^-$) (FIGS. 13A and 13B) by the previously studied spill-over process [D. Degler, et al, *ACS Sens.,* 2016, 11, 1322-1329—incorporated herein by reference in its entirety]. These charged oxygen adsorbates are formed by the extraction of electrons from the conduction band of $SnO_2$, leading to the creation of an electron-depleted region as shown in FIGS. 13A and 13B. In addition to the spill-over process and the presence of Au-nanoparticles whose work function is different from that of $SnO_2$ (q$\varphi$=5.1 eV for Au vs. q$\varphi$=4.8 eV for $SnO_2$), the natural flow of free electrons ensues from the conduction band of $SnO_2$ to that of Au on the surface of the $SnO_2$ leading to the creation of two distinct depletion layers on the $SnO_2$ surface: one on the free surface of $SnO_2$, which is due to oxygen ions, and the other at the immediate interface of Au nanoparticles and SnO$_2$. Exposure to an oxidizing gas (such as NO$_2$) to such a surface causes adsorption of NO$_2$ molecules, followed by a quick reaction with oxygen ions such as O$^-$ or O$^{2-}$, leading to the extraction of more electrons from the conduction band of SnO$_2$ by the following reactions [D. L. Kamble, "Characterization and NO$_2$ gas sensing properties of spray pyrolyzed SnO$_2$ thin films," *Journal of Analytical and Applied Pyrolysis* 127 (2017) 38-46—incorporated herein by reference in its entirety]:

$$O_2(gas) \rightarrow O_2(ads),$$

$$O_2(ads) + e^- \rightarrow O_2^-(ads),$$

$$O_2^-(ads) + e^- \rightarrow 2O^-(ads),$$

$$2O^-(ads) + e^- \rightarrow O^{2-}(ads)$$

$$NO_2(gas) + e^- \rightarrow NO_2^-(ads)$$

$$NO_2^-(ads) + O^-(ads) + 2e^- \rightarrow NO(gas) + 2O^{2-}(ads)$$

These processes will inevitably change the charge density near the surface of SnO$_2$ and lead to increase in the surface-active sites (oxygen ions), which demonstrate noticeable improvement in the response towards NO$_2$.

The invention claimed is:

1. A room temperature nitrogen dioxide gas sensor, comprising:
    at least two electrodes on a substrate, the electrodes separated by 100-500 µm;
    a SnO$_2$ layer in contact with the at least two electrodes on the substrate; and
    gold nanoparticles dispersed on the SnO$_2$ layer, the gold nanoparticles having an average longest dimension of 250-650 nm,
    wherein the substrate has a planar side with a surface area of 0.5-10 cm$^2$,
    wherein the gold nanoparticles consist essentially of gold and are elongated with an aspect ratio in a range of 1.20:1-4:1,
    wherein the gold nanoparticles have an average nearest neighbor distance of 250-500 nm, and
    wherein the SnO$_2$ layer consists essentially of SnO$_2$ and has an average thickness of 10 nm-1,000 nm.

2. The room temperature nitrogen dioxide gas sensor of claim 1, further comprising smaller gold nanoparticles on the SnO$_2$ layer, the smaller gold nanoparticles having an average longest dimension of 10-160 nm.

3. The room temperature nitrogen dioxide gas sensor of claim 1, wherein the gold nanoparticles are dispersed on the SnO$_2$ layer at a surface density of 2×10$^5$-2×10$^{15}$ gold nanoparticles per m$^2$.

4. The room temperature nitrogen dioxide gas sensor of claim 1, further comprising a computing device configured to transmit a data measurement.

5. The room temperature nitrogen dioxide gas sensor of claim 1, wherein the SnO$_2$ is polycrystalline, having an average grain size in a range of 6-10 nm.

6. The room temperature nitrogen dioxide gas sensor of claim 1, wherein the substrate has a surface roughness RMS in a range of 20-50 nm.

7. The room temperature nitrogen dioxide gas sensor of claim 1, wherein the at least two electrodes have an average thickness of 200-400 nm and comprise graphene.

8. A method of determining a concentration of nitrogen dioxide gas with the room temperature nitrogen dioxide gas sensor of claim 1, wherein the room temperature nitrogen dioxide gas sensor further comprises a computing device connected to the at least two electrodes,
    the method comprising:
    contacting the gold nanoparticles with a first gas sample substantially free of nitrogen dioxide gas and measuring a first resistivity across the at least two electrodes;
    contacting the gold nanoparticles with a second gas sample comprising a concentration of nitrogen dioxide gas and measuring a second resistivity across the at least two electrodes;
    determining a response factor, which is the percentage difference of the first resistivity to the second resistivity, relative to the second resistivity; and
    calculating the concentration of nitrogen dioxide gas in the second gas sample based on the response factor,
    wherein the determining and calculating are performed by the computing device.

9. The method of claim 8, wherein during the second contacting, the second gas sample comprises 100 ppb-1800 ppm nitrogen dioxide gas.

10. The method of claim 8, wherein during the first contacting, the first gas sample comprises 300-12,000 ppm of at least one gas selected from the group consisting of H$_2$, NH$_3$, CO$_2$, n-butane, pentane, pentene, O$_2$, and N$_2$.

11. The method of claim 8, wherein during the second contacting, the second resistivity has a response time of 30-180 s.

12. The method of claim 8, wherein during the first contacting, the first gas sample comprises 0.1-99 vol % of at least one gas selected from the group consisting of O$_2$, CO$_2$, H$_2$O, Ar, and N$_2$, relative to a total volume of the first gas sample, or the first gas sample consists essentially of O$_2$, CO$_2$, H$_2$O, Ar, and/or N$_2$.

13. The method of claim 8, wherein during the second contacting, the room temperature nitrogen dioxide gas sensor is located in a neonatal intensive care unit.

14. The method of claim 8, further comprising transmitting the response factor by the computing device.

15. The method of claim 8, which has a repeatability of at least 99% in determining the concentration of nitrogen dioxide gas in the second gas sample.

16. The method of claim 8, wherein during the first contacting, the first gas sample has a temperature of 0-50° C. and a pressure of 0.9-1.1 atm.

17. The method of claim 16, wherein the first gas sample has a temperature of 20-37° C.

18. A method of making a room temperature nitrogen dioxide gas sensor, wherein the room temperature nitrogen gas sensor comprises:
    at least two electrodes on a substrate, the electrodes separated by 100-500 µm;
    a SnO$_2$ layer in contact with the at least two electrodes on the substrate; and
    gold nanoparticles dispersed on the SnO$_2$ layer, the gold nanoparticles having an average longest dimension of 250-650 nm,
    wherein the substrate has a planar side with a surface area of 0.5-10 cm$^2$,
    wherein the gold nanoparticles consist essentially of gold and are elongated with an aspect ratio in a range of 1.20:1-4:1,
    wherein the gold nanoparticles have an average nearest neighbor distance of 250-500 nm, and
    wherein the SnO$_2$ layer consists essentially of SnO$_2$ and has an average thickness of 10 nm-1,000 nm,
    the method comprising:

sputtering SnO$_2$ onto the at least two electrodes on the substrate to produce a SnO$_2$ layer;

sputtering gold onto the SnO$_2$ layer to produce a gold layer; and annealing the SnO$_2$ layer and the gold layer at 450-650° C. to produce the room temperature nitrogen dioxide gas sensor.

19. The method of claim 18, wherein the gold nanoparticles are not contacted with a surfactant or a template.

20. The method of claim 18, wherein for a wavelength in a range of 350-1,000 nm, the SnO$_2$ layer with the gold layer before the annealing has a transmittance of 0.00-0.15, and wherein for the same wavelength, the room temperature nitrogen dioxide gas sensor has a transmittance of 0.40-0.55.

* * * * *